US012570717B2

(12) United States Patent
Kochenderfer et al.

(10) Patent No.: US 12,570,717 B2
(45) Date of Patent: \*Mar. 10, 2026

(54) ANTI-B-CELL MATURATION ANTIGEN CHIMERIC ANTIGEN RECEPTORS WITH HUMAN DOMAINS

(71) Applicants: The United States of America, as represented by the Secretary, Department of Health and Human Services, Bethesda, MD (US); TeneoBio, Inc., Thousand Oaks, CA (US)

(72) Inventors: James N. Kochenderfer, Bethesda, MD (US); Norris Lam, Silver Spring, MD (US); Nathan Trinklein, Thousand Oaks, CA (US); Katherine E. Harris, Thousand Oaks, CA (US); Shelley Force Aldred, Thousand Oaks, CA (US); Wim Van Schooten, Thousand Oaks, CA (US)

(73) Assignees: The United States of America, as represented by the Secretary, Department of Health and Human Services, Bethesda, MD (US); TeneoBio, Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/524,799

(22) Filed: Nov. 30, 2023

(65) Prior Publication Data

US 2024/0091264 A1     Mar. 21, 2024

Related U.S. Application Data

(63) Continuation of application No. 16/626,991, filed as application No. PCT/US2018/039917 on Jun. 28, 2018, now abandoned.

(Continued)

(51) Int. Cl.
C07K 16/46        (2006.01)
A61K 39/395      (2006.01)
(Continued)

(52) U.S. Cl.
CPC .......... *C07K 14/7051* (2013.01); *A61K 40/11* (2025.01); *A61K 40/31* (2025.01);
(Continued)

(58) Field of Classification Search
None
See application file for complete search history.

(56) References Cited

U.S. PATENT DOCUMENTS 10,465,010 B2     11/2019   Wang et al.
11,427,642 B2 *   8/2022    Trinklein  ........... C07K 16/2878
(Continued)

FOREIGN PATENT DOCUMENTS

CN          106459203 A       2/2017
WO      WO 2013/154760 A1    10/2013
(Continued)

OTHER PUBLICATIONS

Mendel et al., Activated T cells express the OX40 ligand: requirements for induction and costimulatory function, Immunol. 117(2): 196-204, Feb. 2006.*
(Continued)

*Primary Examiner* — Claire Kaufman
(74) *Attorney, Agent, or Firm* — Leydig, Voit & Mayer

(57) ABSTRACT

Provided are chimeric antigen receptors (CARs) having antigen specificity for B-cell Maturation Antigen (BCMA). Also provided are related nucleic acids, recombinant expression vectors, host cells, populations of cells, and pharma-
(Continued)

Days after T cell infusion

→ Untreated
▽ SP6-CD828Z
■ 11D5-3-CD8BBZ
● FHVH33-CD828Z
⊖ FHVH33-CD8BBZ ceutical compositions relating to the CARs. Methods of treating or preventing cancer in a mammal are also provided.

13 Claims, 18 Drawing Sheets

Specification includes a Sequence Listing.

Related U.S. Application Data

(60) Provisional application No. 62/527,556, filed on Jun. 30, 2017.

(51) Int. Cl.

| | |
|---|---|
| *A61K 40/11* | (2025.01) |
| *A61K 40/31* | (2025.01) |
| *A61K 40/42* | (2025.01) |
| *C07K 14/705* | (2006.01) |
| *C07K 14/725* | (2006.01) |

(52) U.S. Cl.
CPC .... *A61K 40/4215* (2025.01); *C07K 14/70517* (2013.01); *C07K 14/70521* (2013.01); *C07K 14/70578* (2013.01); *A61K 2239/31* (2023.05); *A61K 2239/48* (2023.05); *C07K 2317/21* (2013.01); *C07K 2317/569* (2013.01); *C07K 2317/73* (2013.01); *C07K 2319/03* (2013.01); *C07K 2319/33* (2013.01)

(56) References Cited

U.S. PATENT DOCUMENTS

| | | |
|---|---|---|
| 2016/0046724 A1 | 2/2016 | Brogdon et al. |
| 2017/0081411 A1 | 3/2017 | Engels et al. |
| 2020/0078399 A1 | 3/2020 | Fan et al. |
| 2021/0147564 A1 | 5/2021 | Trinklein et al. |

FOREIGN PATENT DOCUMENTS

| | | |
|---|---|---|
| WO | WO 2016/014789 A2 | 1/2016 |
| WO | WO 2017/025038 A1 | 2/2017 |
| WO | WO 2018/237037 A2 | 12/2018 |

OTHER PUBLICATIONS

Noël et al., Global analysis of VHHs framework regions with a structural alphabet, Biochimie, 131:11-19, 2016.*

Saerens et al., Identification of a Universal VHH Framework to Graft Non-canonical Antigen-binding Loops of Camel Single-domain Antibodies J. Mol. Biol. 352:597-607, 2005.*

"A Clinical Study of Legend Biotech BCMA-chimeric Antigen Receptor Technology in Treating Relapsed/Refractory (R/R) Multiple Myeloma Patients," accessed online at <clinicaltrials.gov/ct2/history/NCT03090659?V_1=View#StudyPageTop> on Sep. 26, 2018 (pub. Mar. 20, 2017).

Ali et al., "T cells expressing an anti-B-cell maturation antigen chimeric antigen receptor cause remissions of multiple myeloma," *Blood*, 128(13): 1688-1700 (2016).

Belluci et al., "Graft-versus-tumor response in patients with multiple myeloma is associated with antibody response to BCMA, a plasma-cell membrane receptor," *Blood*, 105(10): 3945-3950 (2005).

Brudno et al., "T Cells Genetically Modified to Express an Anti-B-Cell Maturation Antigen Chimeric Antigen Receptor Cause Remissions of Poor-Prognosis Relapsed Multiple Myeloma," *J Clin Oncol.*, 36(22): 2267-2280 (2018).

Carpenter et al., "B-cell maturation antigen is a promising target for adoptive T-cell therapy of multiple myeloma," *Clin Cancer Res.*, 19(8): 2048-2060 (2013).

Chiu et al., "Hodgkin lymphoma cells express TACI and BCMA receptors and generate survival and proliferation signals in response to BAFF and APRIL," *Blood*, 109(2): 729-739 (2007).

Hermans et al., "The Vital assay: a versatile fluorometric technique for assessing CTL- and NKT-mediated cytotoxicity against multiple targets in vitro and in vivo," *J. Immunol Methods*, 285(1): 25-40 (2004).

International Searching Authority, International Search Report and Written Opinion in International Application No. PCT/US2018/039917, mailed Oct. 11, 2018.

Kalled, "The role of BAFF in immune function and implications for autoimmunity," *Immunol Rev.*, 204: 43-54 (2005).

Kim et al., "Mutational approaches to improve the biophysical properties of human single-domain antibodies", *Biochimica et Biophysica Acta*, vol. 1844, Issue 11, pp. 1983-2001 (2014).

Kochenderfer et al., "Construction and preclinical evaluation of an anti-CD19 chimeric antigen receptor," *J. Immunother.*, 32(7): 689-702 (2009).

Laabi et al., "A new gene, BCM, on chromosome 16 is fused to the interleukin 2 gene by a t(4;16)(q26;p13) translocation in a malignant T cell lymphoma," *EMBO J.*, 11(11): 3897-3904 (1992).

Laabi et al., "The BCMA gene, preferentially expressed during B lymphoid maturation, is bidirectionally transcribed," *Nucleic Acids Res.*, 22(7): 1147-1154 (1994).

Mackay et al., "BAFF and APRIL: a tutorial on B cell survival," *Annu. Rev. Immunol.*, 21: 231-264 (2003).

Martinez-Cingolani et al., "Development of chimeric antigen receptors for multiple myeloma," *Biochem. Soc. Trans.*, 44(2): 397-444 (2016).

Moreaux et al., "BAFF and APRIL protect myeloma cells from apoptosis induced by interleukin 6 deprivation and dexamethasone," *Blood*, 103(8): 3148-3157 (2004).

Neri et al., "Neutralizing B-cell activating factor antibody improves survival and inhibits osteoclastogenesis in a severe combined immunodeficient human multiple myeloma model" *Clin. Cancer Res.*, 13(19): 5903-5909 (2007).

Ng et al., "B cell-activating factor belonging to the TNF family (BAFF)-R is the principal BAFF receptor facilitating BAFF costimulation of circulating T and B cells," *J. Immunol.*, 173(2): 807-817 (2004).

Novak et al., "Expression of BCMA, TACI, and BAFF-R in multiple myeloma: a mechanism for growth and survival," *Blood*, 103(2): 689-694 (2004).

O'Connor et al., "BCMA Is Essential for the Survival of Long-lived Bone Marrow Plasma Cells," *J. Exp. Medicine*, 199(1): 91-97 (2004).

Raab et al., "Multiple myeloma," *Lancet*, 374: 324-329 (2009).

Raje et al., "Anti-BCMA CAR T-Cell Therapy bb2121 in Relapsed or Refractory Multiple Myeloma," *N Engl J Med.*, 380(18): 1726-1737 (2019).

Sadelain et al., "The basic principles of chimeric antigen receptor design", *Cancer Discovery*, 3(4): 388-398 (2013).

Thompson et al., "BAFF binds to the tumor necrosis factor receptor-like molecule B cell maturation antigen and is important for maintaining the peripheral B cell population," *J. Exp. Medicine*, 192(1): 129-135 (2000).

Woof et al., "Human antibody-Fc receptor interactions illuminated by crystal structures," *Nat. Rev. Immunol.*, 4(2): 89-99 (2004).

Yan et al., "Recent Advances in Tumor Therapy with Chimeric Antigen Receptor Modified T Cells", *Medical Review*, 22(22): 4417-4421 (2016).

Jackson et al. "Driving CAR T-cells forward", *Nature Reviews Clinical Oncology*, 13(6): 370-383 (2016).

* cited by examiner

FHVH74-CD8BBZ

FHVH32-CD8BBZ

FHVH33-CD8BBZ

FHVH93-CD8BBZ

FHVH74-CD8ICOSZ

FHVH32-CD8ICOSZ

FHVH33-CD8ICOSZ

FHVH93-CD8ICOSZ

ANTI-B-CELL MATURATION ANTIGEN CHIMERIC ANTIGEN RECEPTORS WITH HUMAN DOMAINS

CROSS-REFERENCE TO RELATED APPLICATIONS

This patent application is a continuation of U.S. patent application Ser. No. 16/626,991, filed Dec. 27, 2019, which is the U.S. National Stage of PCT/US2018/039917, filed Jun. 28, 2018, which claims the benefit of U.S. Provisional Patent Application No. 62/527,556, filed Jun. 30, 2017, each of which is incorporated by reference in its entirety herein.

STATEMENT REGARDING FEDERALLY SPONSORED RESEARCH OR DEVELOPMENT

This invention was made with Government support under project number ZIABC01143905 by the National Institutes of Health, National Cancer Institute. The Government has certain rights in the invention.

THE NAMES OF THE PARTIES TO A JOINT RESEARCH AGREEMENT

The presently claimed invention was made by, or on behalf of, the following parties to a joint research agreement. The parties to the joint research agreement are TeneoBio, Inc. and The United States of America, as represented by the Secretary, Department of Health and Human Services.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 63,979 Byte Extensible Markup Language (XML) file named "769948.XML," dated Nov. 29, 2023.

BACKGROUND OF THE INVENTION

Cancer is a public health concern. Despite advances in treatments such as chemotherapy, the prognosis for many cancers may be poor. For example, therapies for multiple myeloma (MM) may cause remissions, but many patients eventually relapse and die. Accordingly, there exists an unmet need for additional treatments for cancer.

BRIEF SUMMARY OF THE INVENTION

An embodiment of the invention provides a chimeric antigen receptor (CAR) comprising an antigen recognition domain, a transmembrane (TM) domain, and a T cell activation domain, wherein the CAR has antigen specificity for B-cell maturation antigen (BCMA), wherein the antigen recognition domain comprises the amino acid sequences of: (a) SEQ ID NOs: 1-3; (b) SEQ ID NOs: 4-6; (c) SEQ ID NOs: 7-9; or (d) SEQ ID NOs: 10-12.

Further embodiments of the invention provide related nucleic acids, recombinant expression vectors, host cells, populations of cells, and pharmaceutical compositions relating to the CARs of the invention.

Additional embodiments of the invention provide related methods of treating or preventing cancer in a mammal.

BRIEF DESCRIPTION OF THE SEVERAL VIEWS OF THE DRAWING(S)

Figures 1A, 1B, 1C, 1D:
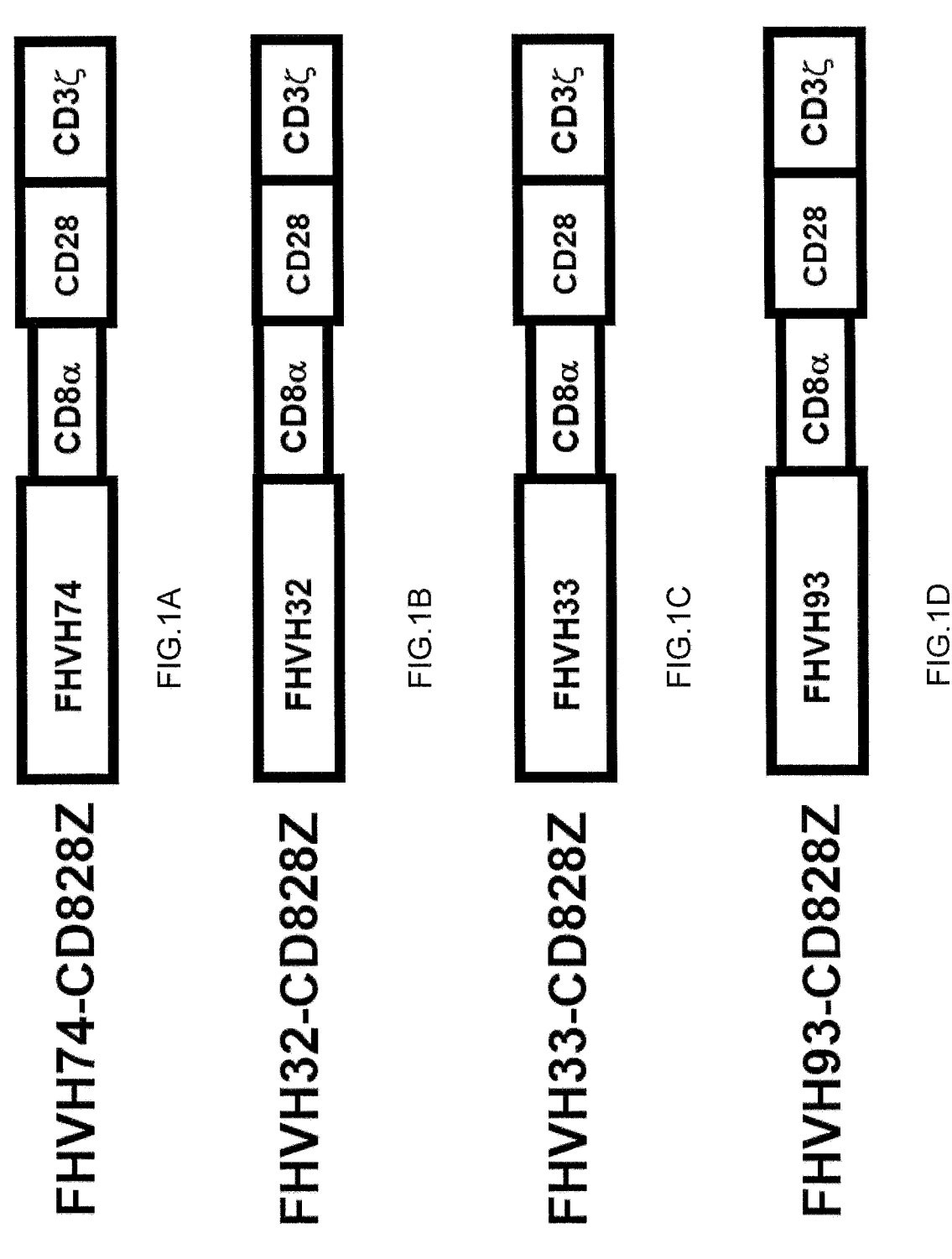
FIGS. 1A-1D are diagrams depicting a CAR comprising the fully-human heavy-chain-only antigen-recognition domains of FHVH74 (A), FHVH32 (B), FHVH33 (C), or FHVH93 (D), in combination with the hinge and transmembrane regions of the CD8α molecule, the cytoplasmic portion of the CD28 costimulatory molecule, and the cytoplasmic portion of the CD3ζ T-cell activation domain.
Figures 1E, 1F, 1G, 1H:
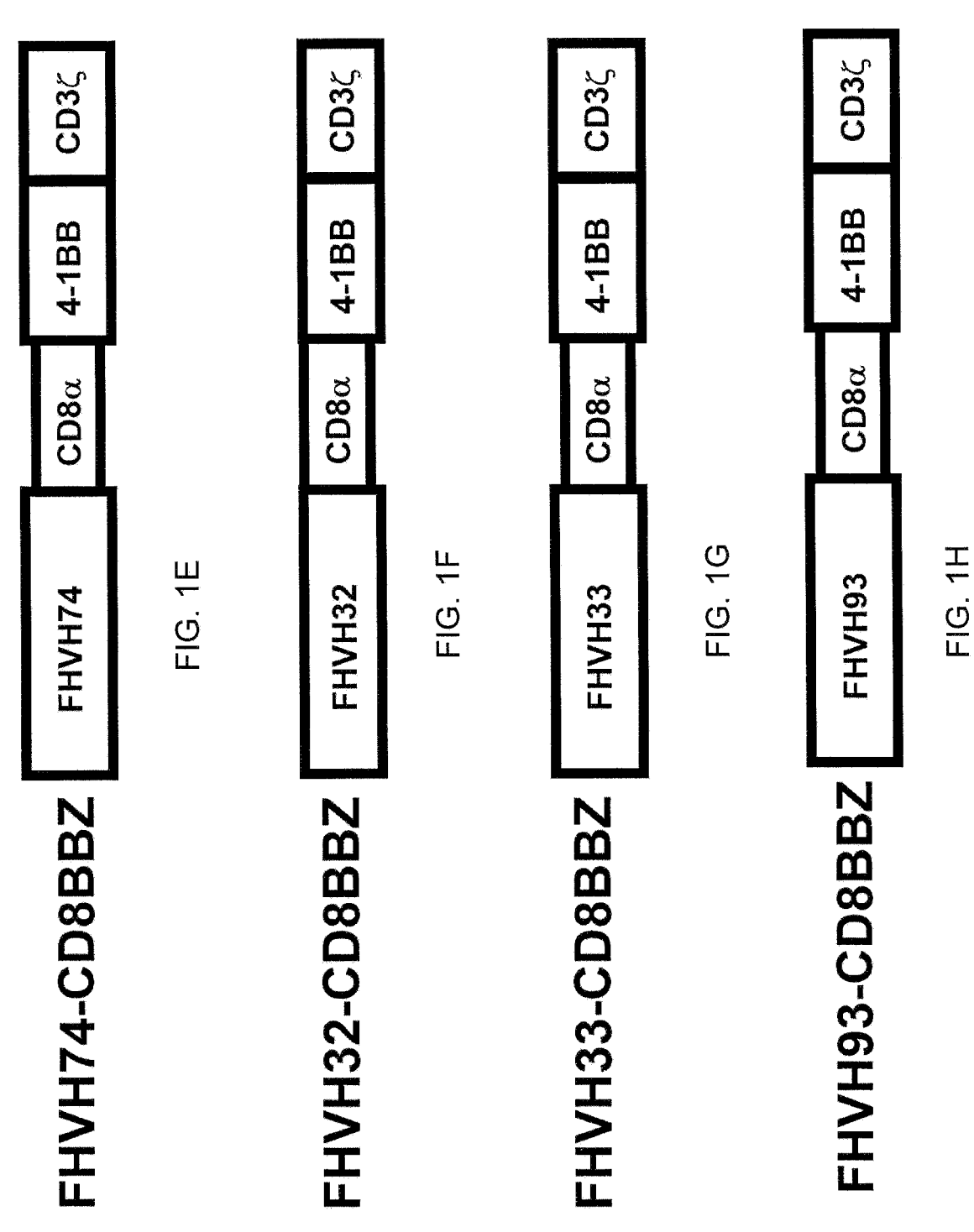
FIGS. 1E-1H are diagrams depicting a CAR comprising the fully-human heavy-chain-only antigen recognition domains of FHVH74 (E), FHVH32 (F), FHVH33 (G), or FHVH93 (H), in combination with the hinge and transmembrane regions of the CD8α molecule, the cytoplasmic portion of the 4-1BB costimulatory molecule, and the cytoplasmic portion of the CD3ζ T-cell activation domain.
Figures 1I, 1J, 1K, 1L:
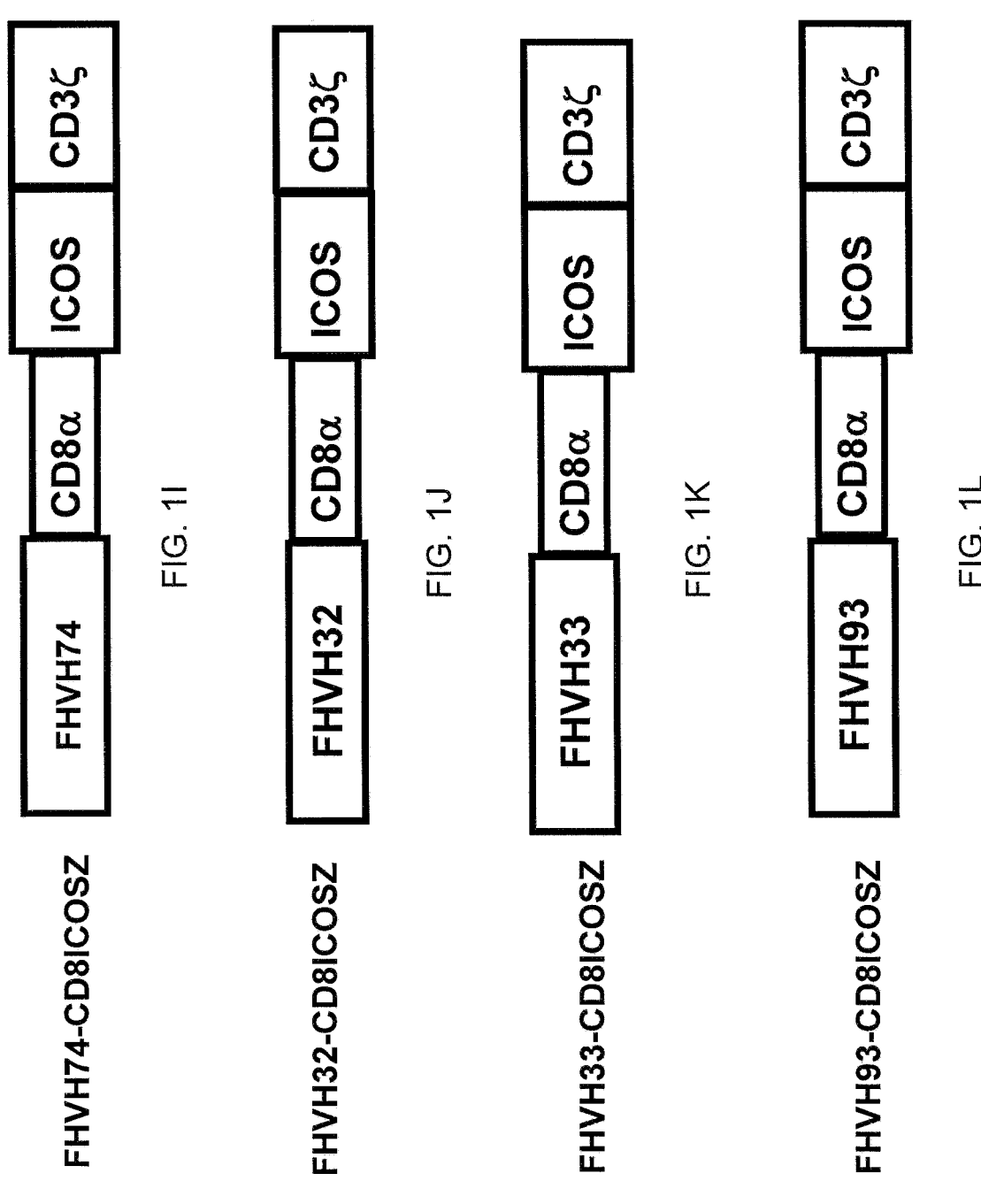
FIGS. 1I-1L are diagrams depicting a CAR comprising the fully-human heavy-chain-only antigen recognition domains of FHVH74 (I), FHVH32 (J), FHVH33 (K), or FHVH93 (L), in combination with the hinge and transmembrane regions of the CD8α molecule, the cytoplasmic portion of the inducible T-cell costimulatory protein (ICOS), and the cytoplasmic portion of the CD3ζ T-cell activation domain.
Figure 2:
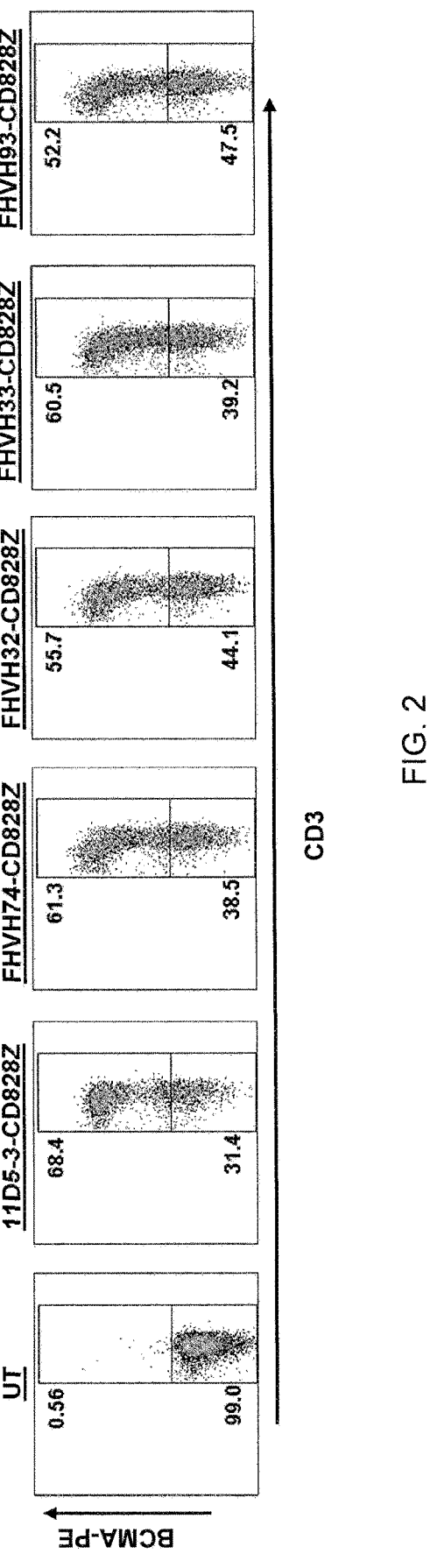

FIG. 2 is a series of graphs which depict experimental data illustrating that the four FHVH CARs shown were expressed by primary human T cells, as described in Example 2. Untransduced (UT) T cells are included as a negative control and 11D5-3-CD828Z is provided as a positive control CAR. The T cells were transduced on day 2 of culture, and the cells were stained with a BCMA-Fc protein reagent on day 7 of culture. The plots are gated on live lymphocytes. The numbers on the plots are the percentages of CD3+ cells expressing the CAR (top) or not expressing the CAR (bottom).

Figure 3:
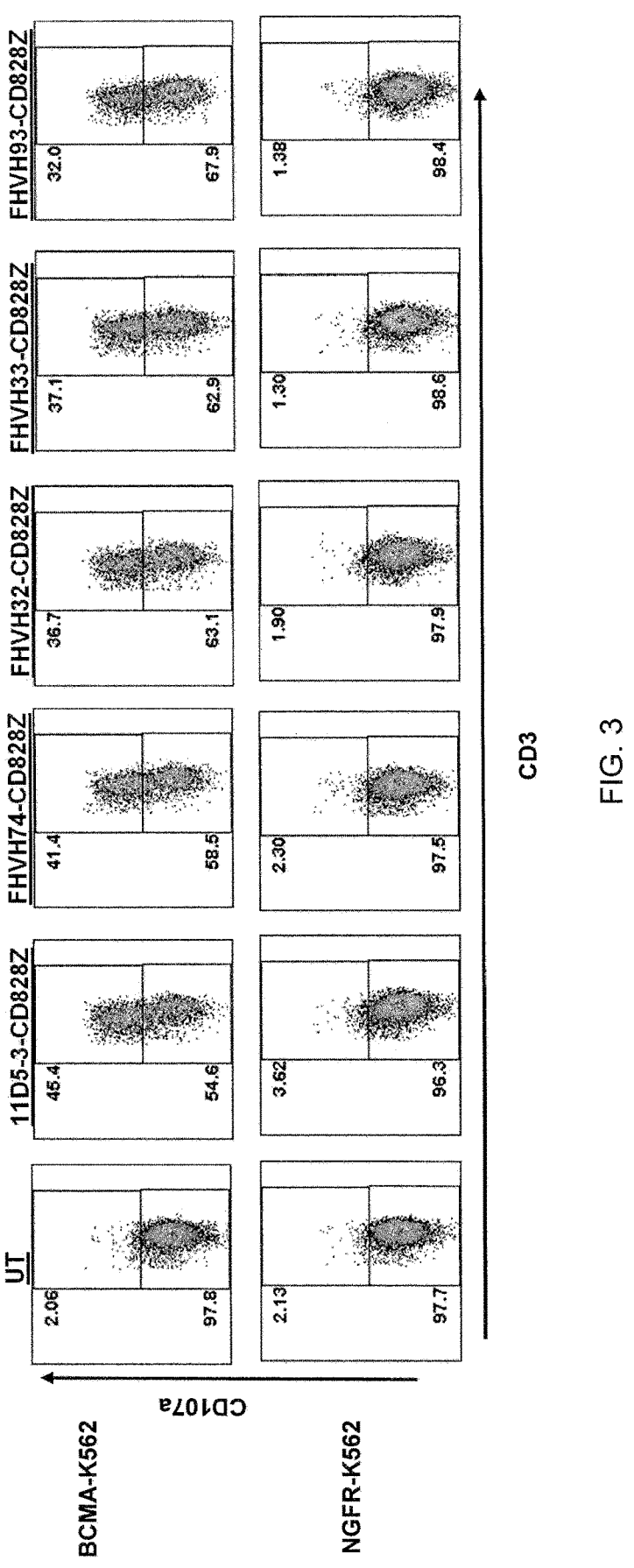

FIG. 3 is a series of graphs which depict experimental data illustrating BCMA-specific degranulation by the FHVH CAR-expressing T cells. The graphs show the results for primary human T cells transduced with one of the four FHVH CARs in a CD107a degranulation assay to assess antigen-specific function. T cells expressing each CAR degranulated to a greater degree when cultured with $BCMA^+$ target cells (BCMA-K562) as compared to BCMA-negative target cells (NGFR-K562), as described in Example 3. UT cells are included as a negative control and 11D5-3-CD828Z is provided as a positive control CAR. The plots are gated on $CD3^+$ lymphocytes. The numbers on the plots are the percentages of CD3+ cells upregulating CD107a (top) or not upregulating CD107a (bottom).

Figures 4A, 4B, 4C:
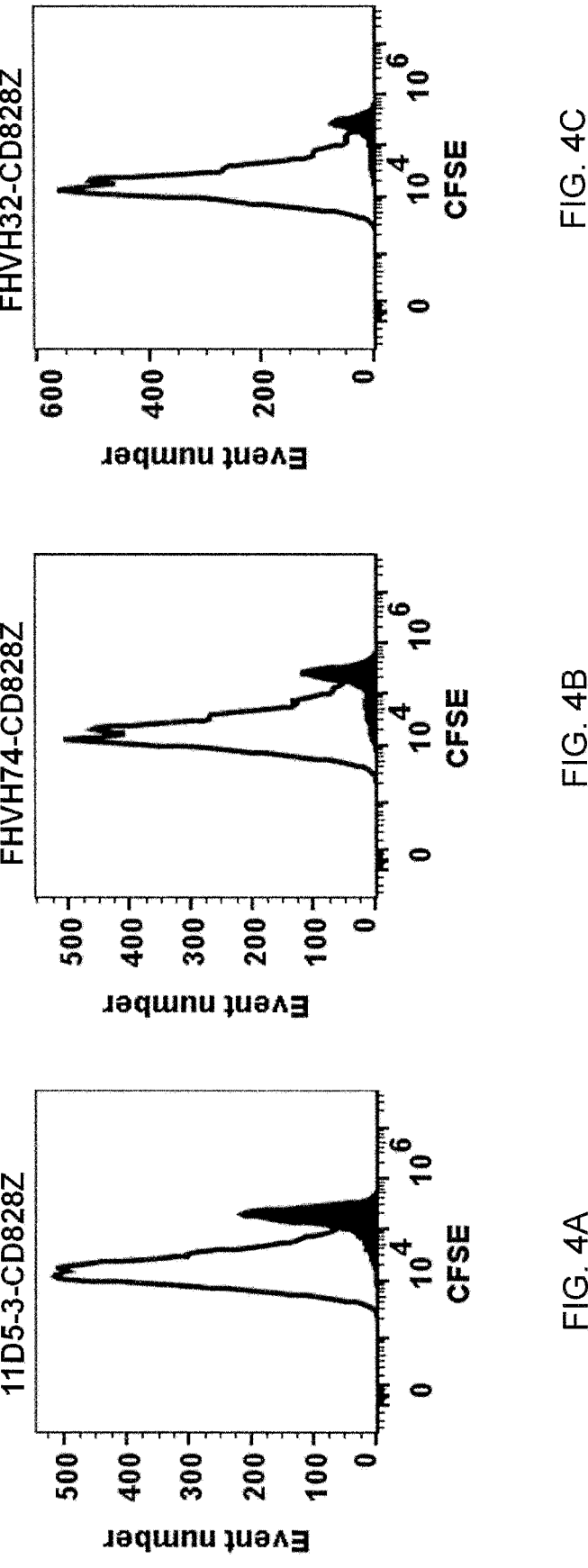

FIG. 4A is a graph which depicts experimental data illustrating that the 11D5-3-CD828Z CAR proliferated in a BCMA-specific manner. Plots are gated on live $CD3^+$ lymphocytes. The open histogram represents $CAR^+$ T cells that were stimulated with BCMA-K562 (BCMA-expressing) target cells, and the black histograms represent $CAR^+$ T cells that were stimulated with NGFR-K562 (BCMA-negative) cells. All results were generated at the same time with cells from the same patient.

FIGS. 4B-4E are graphs which depict experimental data illustrating that the FHVH74-CD828Z (B), FHVH32-CD828Z (C), FHVH33-CD828Z (D), or FHVH93-CD828Z (E) CARs proliferated in a BCMA-specific manner as described in Example 5.

Figure 4F:
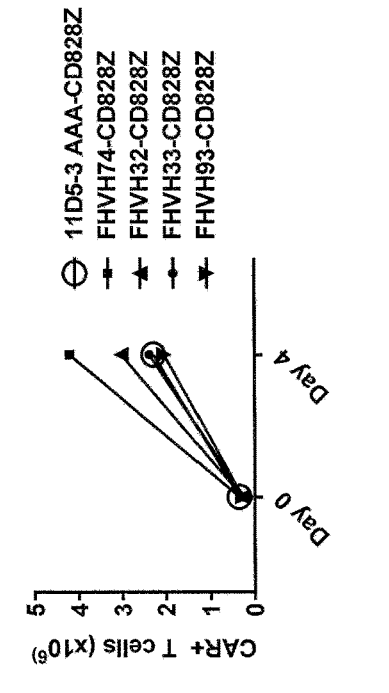
Figure 4E:
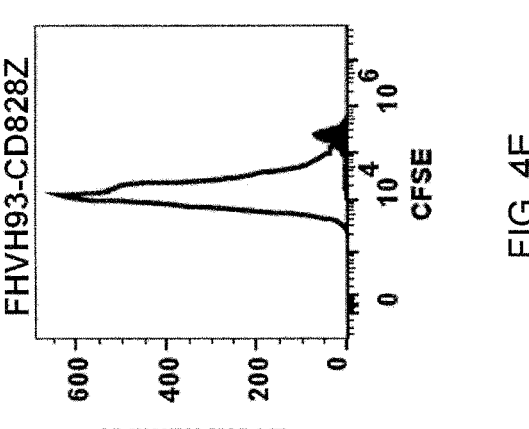
Figure 4D:
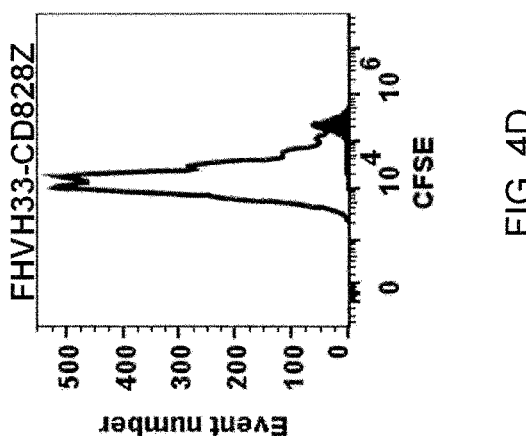
Figures 5A, 5B:

FIG. 4F is a graph which depicts experimental data illustrating that the absolute number of $CAR^+$ T cells increased when the T cells transduced with the indicated CAR were cultured with BCMA⁺ target cells. The number of CAR⁺ T cells increased for T cells expressing all CARs when the CAR T cells were cultured with BCMA-K562 cells. The Y-axis represents the number of CAR⁺ T cells ($\times 10^6$). The X-axis represents the number of days that the T cells were cultured with BCMA⁺ target cells FIG. 5A is a graph which depicts experimental data illustrating the ability of the FHVH33-CD828Z CAR to kill BCMA⁺ target cells, as compared with the ability of UT cells to kill BCMA⁺ target cells. T cells expressing the FHVH33-CD828Z CAR were cultured with RPMI8226 target cells in vitro for four hours at the indicated effector to target ratios. Cytotoxicity was determined in duplicate. The results are displayed as a +/− standard error of the mean. The Y-axis represents the % cytotoxicity of the CARs. The X-axis represents the T-cell to target cell ratio.

FIG. 5B is a graph which depicts experimental data illustrating the ability of the FHVH33-CD8BBZ CAR to kill BCMA⁺ target cells, as compared with the ability of UT cells to kill BCMA⁺ target cells. T cells expressing the FHVH33-CD8BBZ CAR were cultured with RPMI8226 target cells in vitro for four hours at the indicated effector to target ratios. Cytotoxicity was determined in duplicate. The results are displayed as a +/− standard error of the mean. The Y-axis represents the % cytotoxicity of the CARs. The X-axis represents the T-cell to Target cell ratio.

Figure 6:
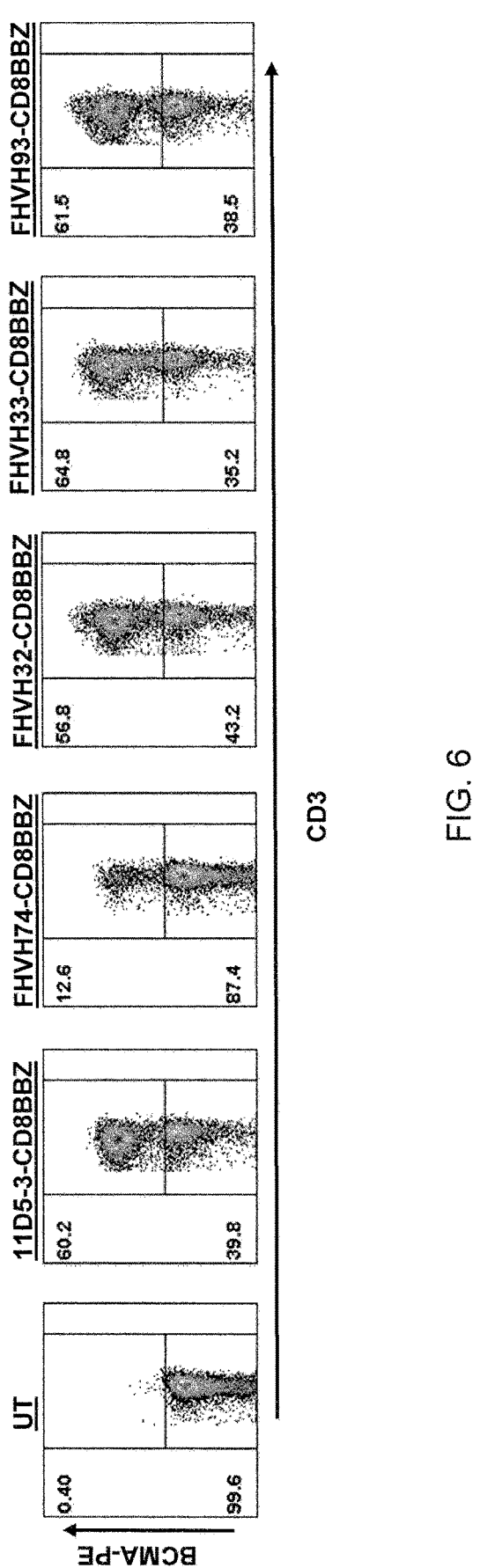

FIG. 6 is a series of graphs which depict experimental data illustrating that CARs with 4-1BB costimulatory domains were expressed on the surface of primary human T cells, with FHVH33-CD8BBZ showing the highest expression. The plots show BCMA-Fc staining of the four FHVH CARs, staining of the 11D5-3-CD828Z control CAR, and staining of UT cells. The plots are gated on live lymphocytes. The numbers on the plots are the percentages of cells staining with (top number) or not staining with (bottom number) BCMA-Fc.

Figure 7B:
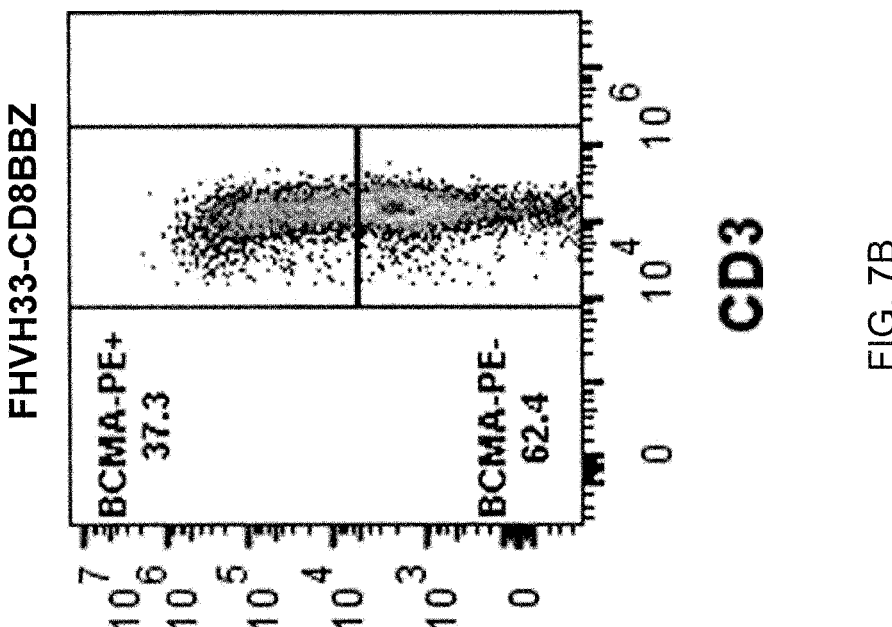
Figure 7A:
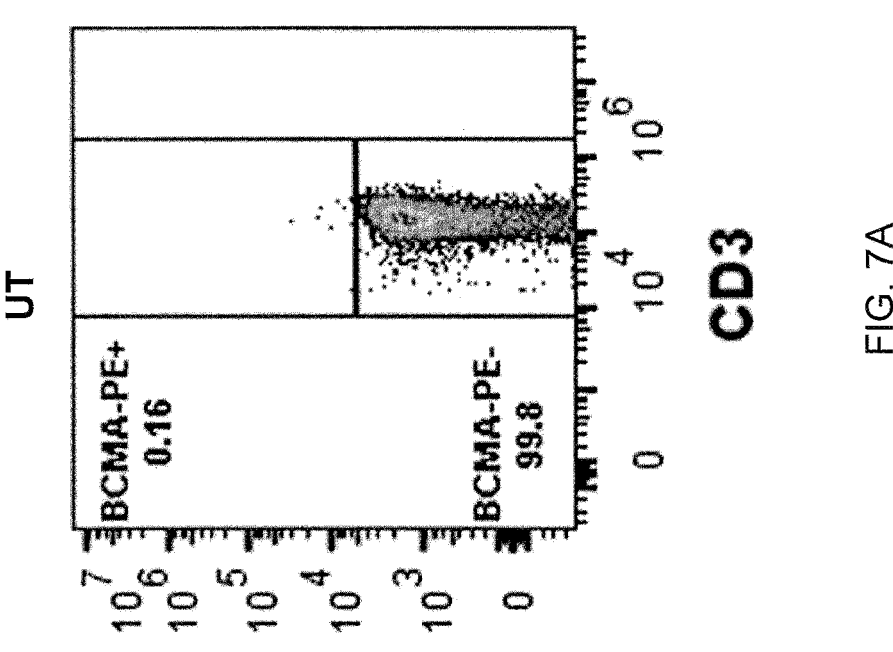
Figure 7D:
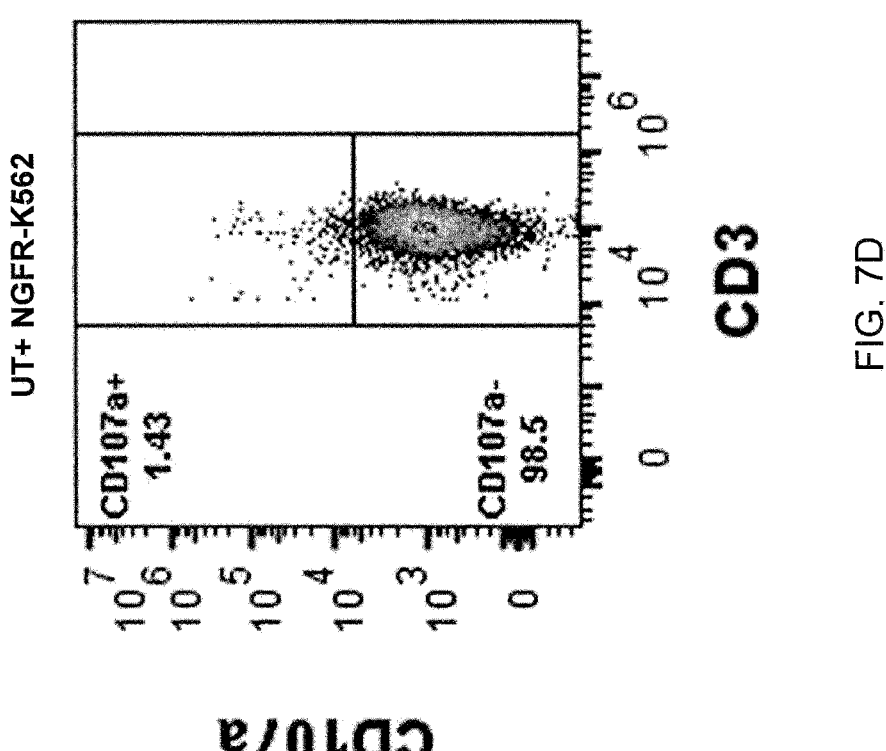
Figure 7C:
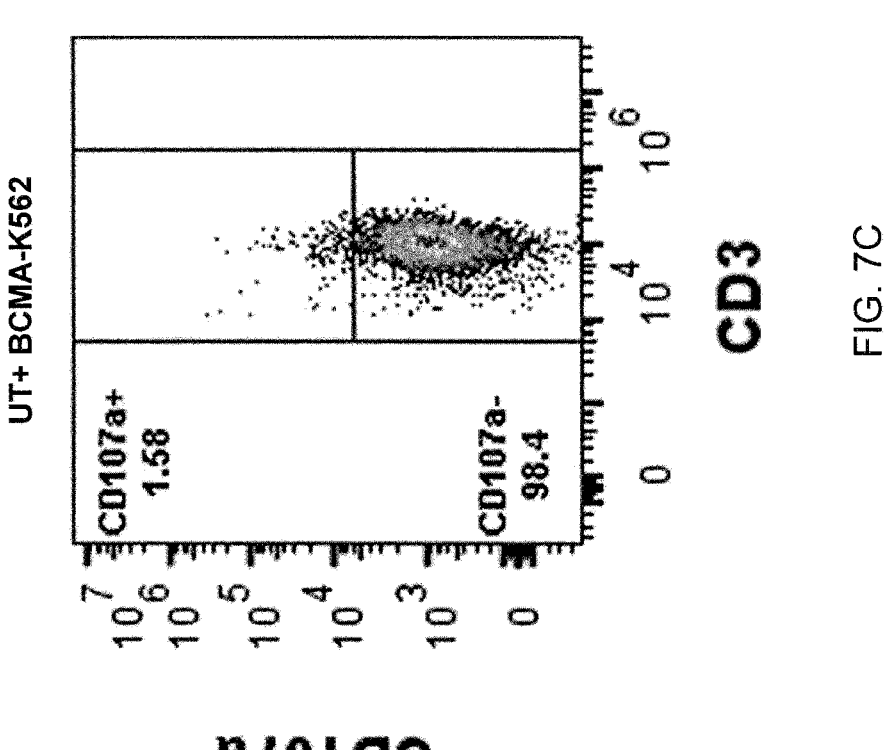
Figure 7F:
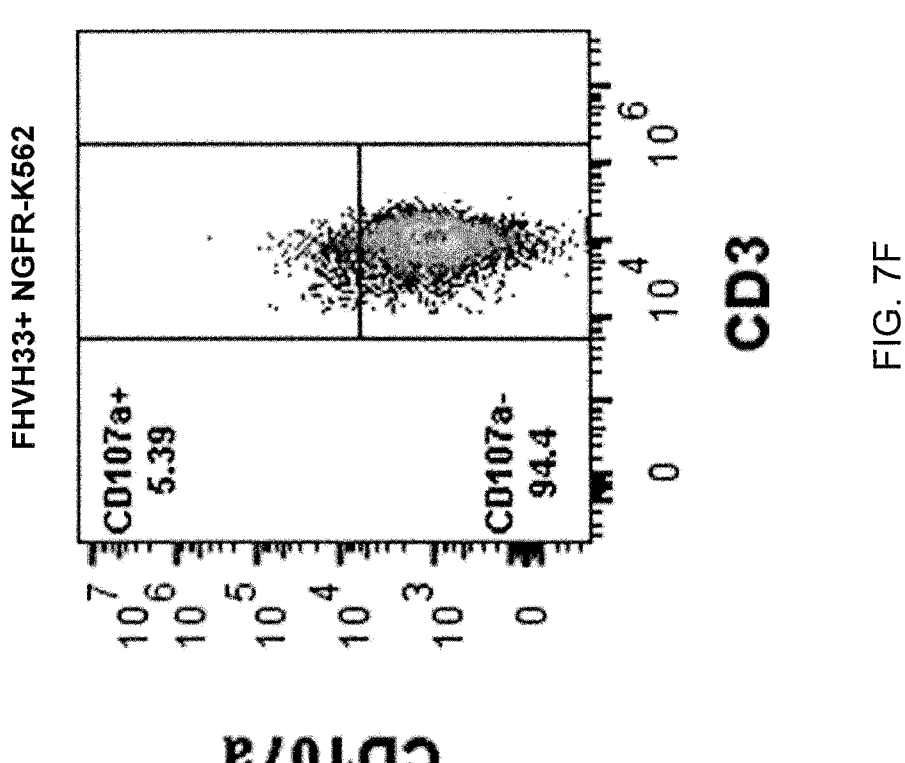
Figure 7E:
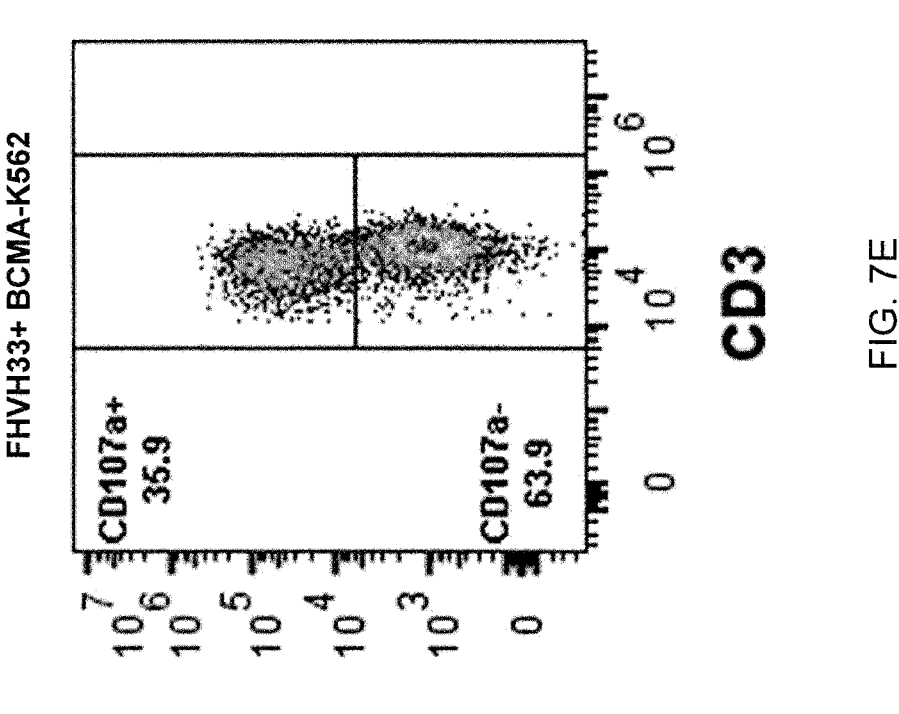

FIGS. 7A-7B depict expression of this CAR in UT cells (A) as compared to FHVH33-CD8BBZ-expressing T cells (B). The plots are gated on live CD3⁺ lymphocytes. The numbers in the plots are the percentages of BCMA-PE+ (top) and BCMA-PE− (bottom).

FIGS. 7C-7F depict experimental data illustrating that T cells transduced with FHVH33-CD8BBZ degranulated in a BCMA-specific manner, as assessed by CD107a staining. The data show upregulation of CD107a in UT+BCMA-K562 (C) and UT+NGFR-K562 cells (D), in comparison with upregulation of CD107a in FHVH33+BCMA-K562 (E) and FHVH33+NGFR-K562 cells (F). The same T cell cultures as were presented in FIGS. 7A-7B were used. Plots are gated on live CD3⁺ lymphocytes. The numbers in the plots are the percentages of CD107a+ (top) and CD107a− (bottom).

Figure 7G:
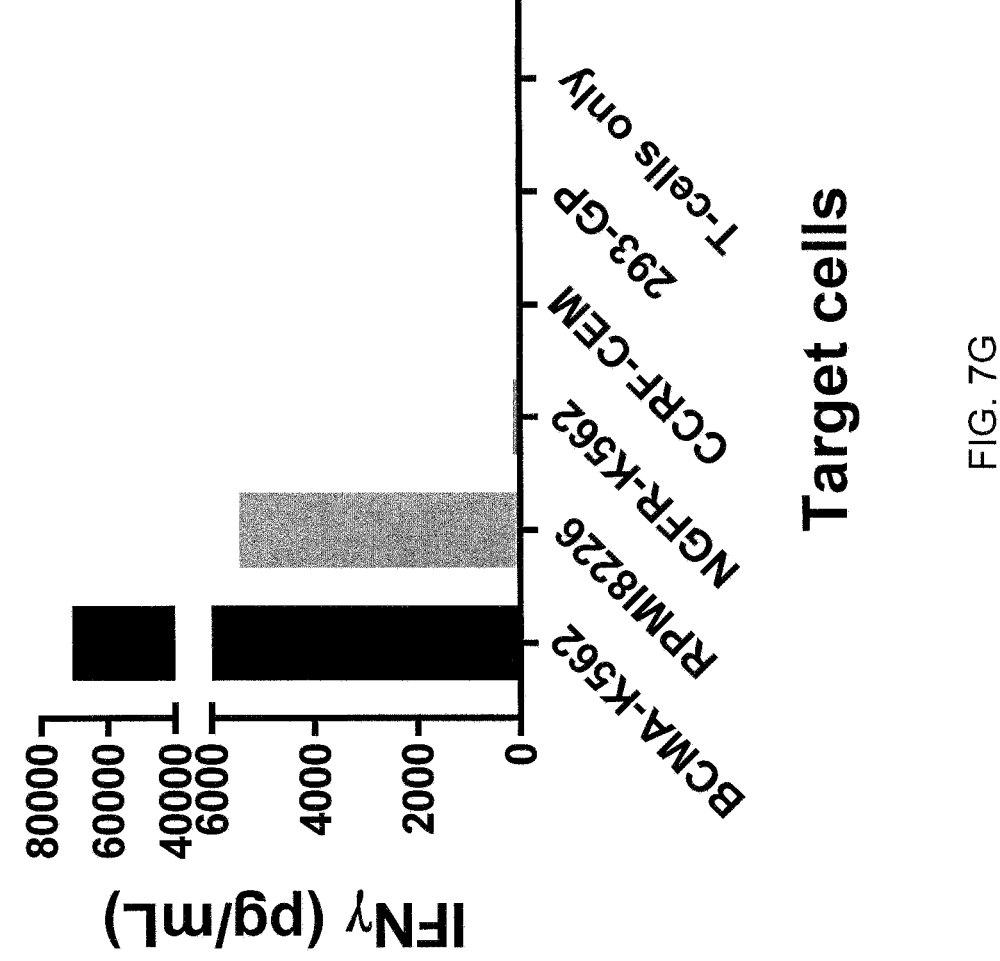

FIG. 7G depicts experimental data illustrating that CAR-expressing T cells produced IFNγ in a BCMA-specific manner. Significant amounts of IFNγ were released when the T cells were cultured with the BCMA⁺ cell lines BCMA-K562 and RPMI8226. The Y-axis represents amount of IFNγ in pg/mL. The X-axis represents the target cells used in the experiments.

Figure 8:
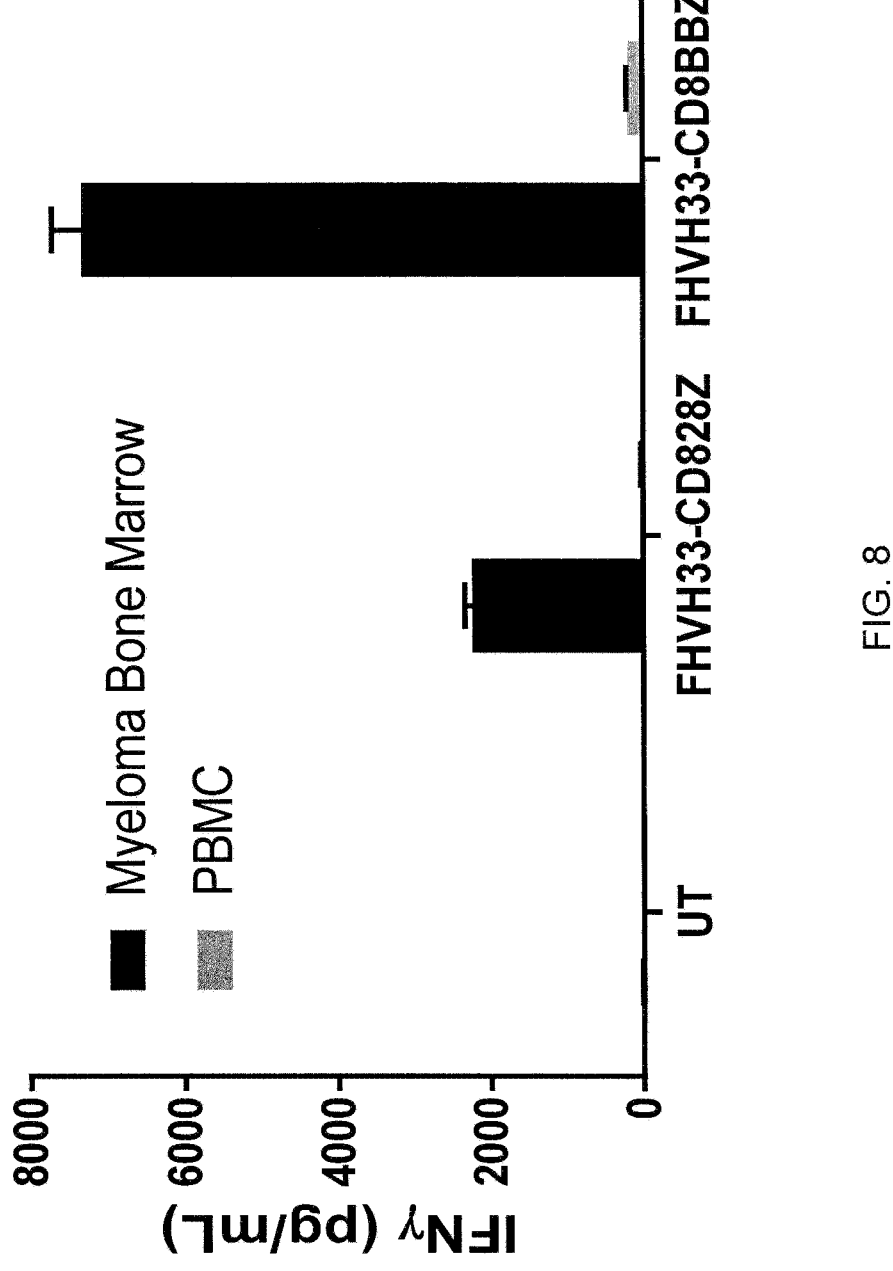

FIG. 8 is a graph showing the amount of IFNγ (pg/ml) secreted by T cells which were untransduced (UT) or transduced with FHVH33-CD828Z or FHVH33-CD8BBZ CAR upon co-culture with target primary human myeloma bone marrow cells (black bars) or control target PBMC (grey bars).

Figure 9A:
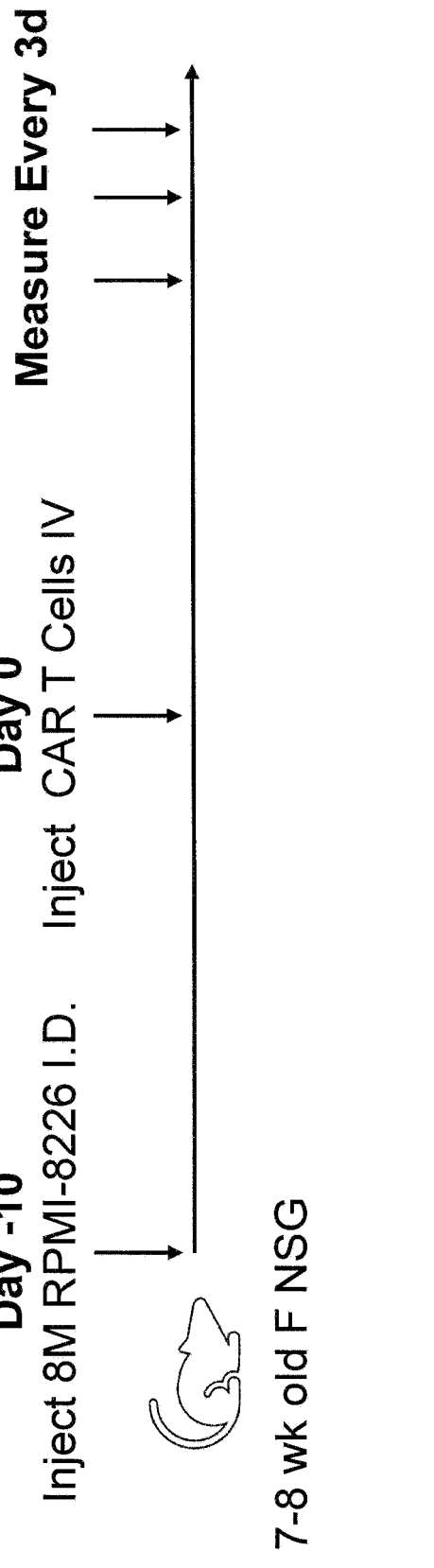

FIG. 9A is a schematic illustrating a dose titration of FHVH33-CD8BBZ T cells in mice. Female (F), 7-8 week (wk) old NSG mice were injected intradermally (i.d.) with eight million (M) RPMI8226 cells and tumors were allowed to grow for 10 days. On day 0, the mice received intravenous (IV) infusions of various numbers of FHVH33-CD8BBZ-expressing T cells. Tumors were measured every third day (d).

Figures 9B, 9C:
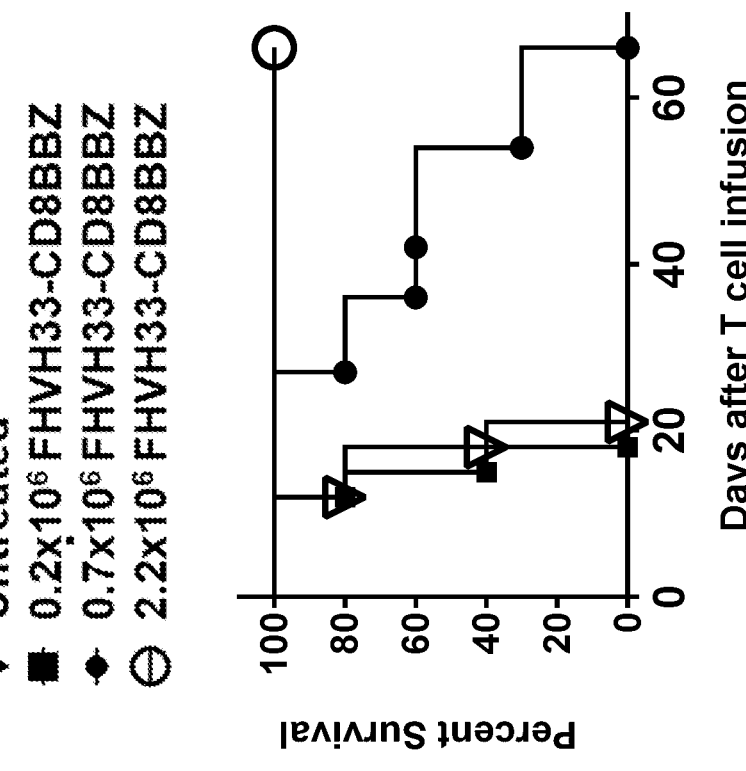

FIG. 9B is a graph showing the tumor volume (mm³) measured in mice treated as shown in FIG. 9A with $0.2\times10^6$ (closed triangles), $0.7\times10^6$ (closed circles), or $2.2\times10^6$ (open circles) FHVH33-CD8BBZ-expressing T cells at the indicated number of days following CAR T cell infusion. Untreated mice are represented by open triangles.

FIG. 9C is a graph showing the percent survival of the mice shown in FIG. 9B following treatment with $0.2\times10^6$ (closed squares), $0.7\times10^6$ (closed circles), or $2.2\times10^6$ (open circles) FHVH33-CD8BBZ-expressing T cells at the indicated number of days following CAR T cell infusion. Untreated mice are represented by open triangles.

Figure 10A:
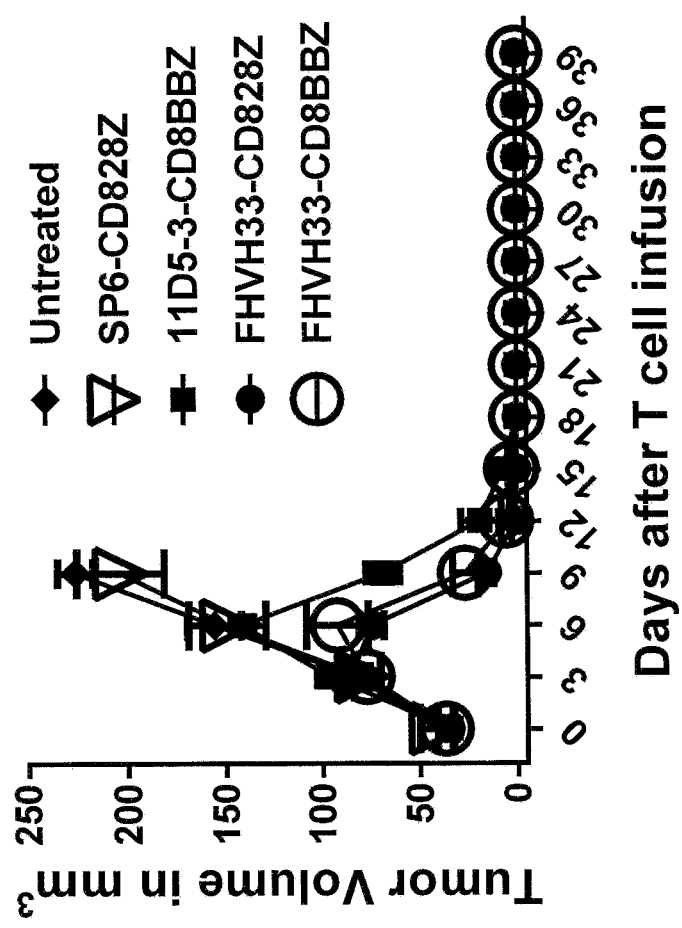

FIG. 10A is a graph showing the tumor volume (mm³) measured in mice treated with T cells expressing the SP6-CD828Z (triangles), 11D5-3-CD8BBZ (squares), FHVH33-CD8BBZ (open circles), or FHVH33-CD828Z (closed circles) CAR at the indicated number of days following CAR T cell infusion. Untreated mice are represented by diamonds.

Figure 10B:
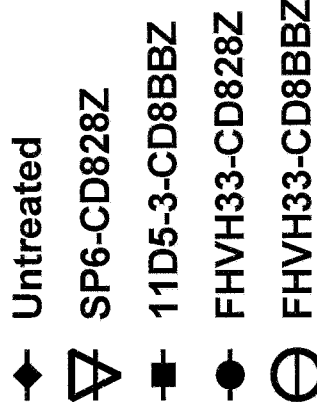
Figure 10B:
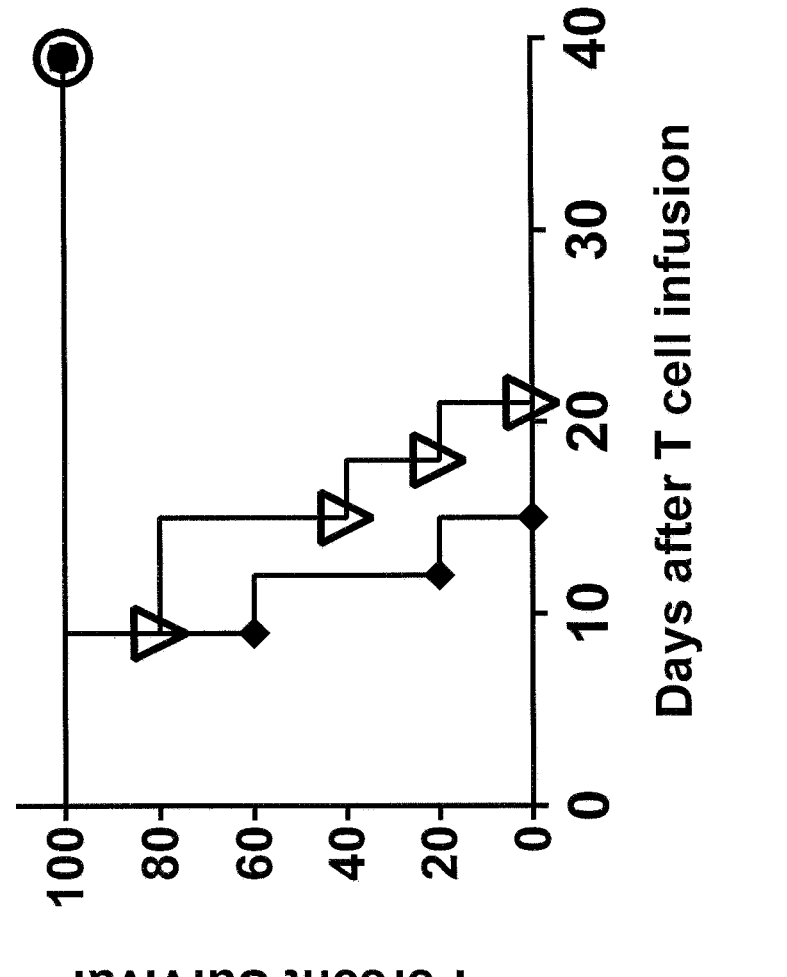

FIG. 10B is a graph showing the percent survival of mice treated with T cells expressing the SP6-CD828Z (triangles), 11D5-3-CD8BBZ (squares), FHVH33-CD8BBZ (open circles), or FHVH33-CD828Z (closed circles) CAR at the indicated number of days following CAR T cell infusion. Untreated mice are represented by diamonds.

DETAILED DESCRIPTION OF THE INVENTION

An embodiment of the invention provides a CAR comprising an antigen recognition domain, a TM domain, and a T cell activation domain, wherein the CAR has antigen specificity for BCMA. A CAR is an artificially constructed hybrid protein or polypeptide containing an antigen recognition domain of an antibody linked to T-cell signaling or T-cell activation domains. CARs have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains.

The inventive CARs have antigen specificity for B-cell Maturation Antigen (BCMA, also known as CD269). BCMA is a member of the tumor necrosis factor receptor superfamily (see, e.g., Thompson et al., *J. Exp. Medicine,* 192(1): 129-135 (2000), and Mackay et al., *Annu. Rev. Immunol.,* 21: 231-264 (2003)). BCMA binds B-cell activating factor (BAFF) and a proliferation inducing ligand (APRIL) (see, e.g., Mackay et al., supra, and Kalled et al., *Immunological Reviews,* 204: 43-54 (2005)). Among non-malignant cells, BCMA has been reported to be expressed mostly in plasma cells and subsets of mature B-cells (see, e.g., Laabi et al., *EMBO J.,* 11(11): 3897-3904 (1992); Laabi et al., *Nucleic Acids Res.,* 22(7): 1147-1154 (1994); Kalled et al., supra; O'Connor et al., *J. Exp. Medicine,* 199(1): 91-97 (2004); and Ng et al., *J. Immunol.,* 173(2): 807-817 (2004)). BCMA RNA has been detected universally in multiple myeloma cells, and BCMA protein has been detected on the surface of plasma cells from multiple myeloma patients by several investigators (see, e.g., Novak et al., *Blood*, 103(2): 689-694 (2004); Neri et al., *Clinical Cancer Research*, 13(19): 5903-5909 (2007); Bellucci et al., *Blood*, 105(10): 3945-3950 (2005); and Moreaux et al., *Blood*, 103(8): 3148-3157 (2004)). BCMA expression has also been detected on the surface of Hodgkin's lymphoma cells (see, e.g., Chiu et al., *Blood*, 109(2): 729-739 (2007)). Human BCMA has the amino acid sequence of SEQ ID NO: 42.

The phrases "has antigen specificity" and "elicit antigen-specific response," as used herein, means that the CAR can specifically bind to and immunologically recognize an antigen, such that binding of the CAR to the antigen elicits an immune response.

The inventive CARs may provide any one or more of a variety of advantages. For example, the inventive CARs may provide reduced anti-CAR immunogenicity. CARs comprising one or both of non-human domains (e.g., mouse domains) and artificial linker peptide may elicit an anti-CAR immune response upon administration to a patient. Such anti-CAR immune responses may reduce the persistence of the CAR-expressing cells and reduce or eliminate the effectiveness of the CAR therapy. Without being bound to a particular theory or mechanism, it is believed that any one or more of the following features of the inventive CARs may reduce or eliminate potential sources of anti-CAR immunogenicity: (i) all domains of the CAR are human; (ii) the CAR does not comprise an artificial linker peptide, e.g., a linker peptide having a length of about 10 to about 25 amino acid residues and consisting of any one or more of glycine, serine, and threonine; (iii) the CAR does not comprise an antibody light chain variable region; and (iv) the antigen recognition domain comprises no more than a single antibody heavy chain variable region. Reducing or eliminating potential sources of anti-CAR immunogenicity is believed to improve that persistence of CAR-expressing cells and the effectiveness of the CAR therapy. Moreover, any one or more of the foregoing features (ii)-(iv) may facilitate the preparation of CARs which target one or more different antigens (other than BCMA) in addition to BCMA.

The inventive CARs may have less anti-CAR immunogenicity as compared to traditional CARs. Traditional CARs may have any one or more of the following features: (i) not all of the domains of the traditional CAR are human; (ii) the traditional CAR comprises an artificial linker peptide, e.g., a linker peptide having a length of about 10 to about 25 amino acid residues and consisting of any one or more of glycine, serine, and threonine; and (iii) the traditional CAR comprises an antibody light chain variable region (hereinafter referred to as, "traditional CARs").

The anti-CAR immunogenicity is reduced in accordance with the invention if the immune response to the inventive CAR is diminished, quantitatively or qualitatively, as compared to the immune response to a traditional CAR. A quantitative decrease in anti-CAR immunogenicity encompasses a decrease in the magnitude or degree of the anti-CAR immune response. The magnitude or degree of anti-CAR immunogenicity can be measured on the basis of any number of known parameters, such as a decrease in the level of cytokine (e.g., CAR-specific cytokine) production (cytokine concentration), a decrease in the number of lymphocytes activated (e.g., proliferation of lymphocytes (e.g., CAR-specific lymphocytes)) or recruited, and/or a decrease in the production of antibodies (CAR-specific antibodies) (antibody concentration), a decrease in the ability of host (recipient) T cells to kill CAR-expressing T cells, etc. A qualitative decrease in anti-CAR immunogenicity encompasses any change in the nature of the anti-CAR immune response that renders the anti-CAR immune response less effective at mediating the reduction of the cytotoxic activity of the CAR. Methods of measuring anti-CAR immunogenicity are known in the art. For example, measuring the types and levels of cytokines produced can measure anti-CAR immunogenicity. Reduced anti-CAR immunogenicity may be characterized by a decrease in the production of cytokines such as any one or more of IFN-γ, TNF-α, and granzyme B, and/or a reduced stimulation of a cell-mediated anti-CAR immune response, such as a decrease in the proliferation and activation of T-cells and/or macrophages specific for the inventive CAR as compared to that obtained with a traditional CAR. Reduced anti-CAR immunogenicity may be characterized by any one or more of a decrease in anti-CAR T cell stimulation, an decrease in anti-CAR T cell proliferation, a decrease in anti-CAR T cell IFNγ and/or granzyme B secretion, and a decrease in the ability of host T cells to kill CAR-expressing T cells. Qualitative and quantitative diminishment of anti-CAR immunogenicity can occur simultaneously, and are not mutually exclusive. The phrase "anti-CAR immunogenicity," as used herein, refers to the immune response against the CAR itself and not to any aspect of the immune response against the target antigen BCMA which the CAR may provide.

The CAR comprises an antigen recognition domain. The antigen recognition domain recognizes and binds to BCMA. In an embodiment of the invention, the antigen recognition domain comprises a heavy chain variable region of a human anti-BCMA antibody. A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The VH and VL regions have the same general structure, with each region comprising four framework regions, whose sequences are relatively conserved. The framework regions are connected by three complementarity determining regions (CDRs), namely, CDR1, CDR2, and CDR3. However, as explained above, in an embodiment of the invention, the CAR does not comprise an antibody light chain variable region. Accordingly, in an embodiment of the invention, the antigen recognition domain comprises no more than a single antibody heavy chain variable region.

In an embodiment, the antigen recognition domain comprises the CDR1 region, the CDR2 region, and the CDR3 region of the heavy chain variable region of a human anti-BCMA antibody. In this regard, in an embodiment of the invention, the antigen recognition domain may comprise:

(a) one or more of a heavy chain CDR1 region comprising SEQ ID NO: 1; a heavy chain CDR2 region comprising SEQ ID NO: 2; and a heavy chain CDR3 region comprising SEQ ID NO: 3 (the CDR regions of the FHVH74 heavy chain variable region);

(b) one or more of a heavy chain CDR1 region comprising SEQ ID NO: 4; a heavy chain CDR2 region comprising SEQ ID NO: 5; and a heavy chain CDR3 region comprising SEQ ID NO: 6 (the CDR regions of the FHVH32 heavy chain variable region);

(c) one or more of a heavy chain CDR1 region comprising SEQ ID NO: 7; a heavy chain CDR2 region comprising SEQ ID NO: 8; and a heavy chain CDR3 region comprising SEQ ID NO: 9 (the CDR regions of the FHVH33 heavy chain variable region); or (d) one or more of a heavy chain CDR1 region comprising SEQ ID NO: 10; a heavy chain CDR2 region comprising SEQ ID NO: 11; and a heavy chain CDR3 region comprising SEQ ID NO: 12 (the CDR regions of the FHVH93 heavy chain variable region).

Preferably, the antigen recognition domain comprises the amino acid sequences of (a) all of SEQ ID NOs: 1-3; (b) all of SEQ ID NOs: 4-6; (c) all of SEQ ID NOs: 7-9; or (d) all of SEQ ID NOs: 10-12.

In an embodiment of the invention, the antigen recognition domain comprises the heavy chain variable region of a human anti-BCMA antibody. In this regard, the antigen recognition domain may comprise the amino acid sequence of (a) SEQ ID NO: 13 (FHVH74 heavy chain variable region), (b) SEQ ID NO: 14 (FHVH32 heavy chain variable region), (c) SEQ ID NO: 15 (FHVH33 heavy chain variable region), or (d) SEQ ID NO: 16 (FHVH93 heavy chain variable region).

In an embodiment of the invention, the antigen recognition domain does not comprise a linker peptide. The antigen recognition domains of traditional CARs may be composed of single chain variable fragments (scFv). An scFv is a monovalent molecule including the two domains of the Fv fragment (i.e., VL and VH) joined by an artificial linker peptide which enables the two domains to be synthesized as a single polypeptide chain. Any one or more of the following features of the inventive CARs may, advantageously, reduce or eliminate potentially immunogenic junctions that join different components of the CAR, e.g., the two potentially immunogenic junctions that join the linker peptide to the VL and VH of the scFvs employed in traditional CARs: (i) the lack of a linker peptide, such as that which is typically found in scFvs employed in traditional CARs, (ii) the lack of an antibody light chain variable region (which are also employed in traditional CARs), and (iii) the presence of no more than a single antibody heavy chain variable region. The junctions and the linker peptide(s) may be immunogenic because they are artificial sequences not normally found in humans. Alternatively or additionally, any one or more of the foregoing features (i)-(iii) may eliminate any potentially immunogenic regions in one or both of the peptide liker and the antibody light chain variable region. The purpose of the linker peptide is generally to form a flexible link between two other peptides or proteins (e.g., between an antibody heavy chain and an antibody light chain). The linker peptide may be of any length and many comprise any amino acid sequence. In an embodiment of the invention, the linker peptide may have a length of about 5 to about 100 amino acid residues, about 8 to about 75 amino acid residues, about 8 to about 50 amino acid residues, about 10 to about 25 amino acid residues, about 8 to about 30 amino acid residues, about 8 to about 40 amino acid residues, or about 8 to about 50 amino acid residues. In an embodiment of the invention, the antigen recognition domain does not comprise a linker peptide having a length of about 8 to about 40 amino acid residues. For example, the linker peptide may comprise or consist of any one or more of glycine, serine, threonine, with or without other amino acid residues. In an embodiment of the invention, the antigen recognition domain does not comprise a linker peptide having a length of about 8 to about 40 amino acid residues and consisting of any one or more of glycine, serine, and threonine.

In another embodiment, the inventive CAR comprises a leader domain. The leader domain may be positioned at the amino terminus of the antigen recognition domain (e.g., the heavy chain variable region of the anti-BCMA antibody). The leader domain may comprise any suitable leader sequence. Preferably, the leader domain is a human leader domain. In one embodiment, the leader domain is a human granulocyte-macrophage colony-stimulating factor (GM-CSF) receptor sequence or a human CD8α leader sequence.

In another embodiment, the CAR comprises a hinge domain. One of ordinary skill in the art will appreciate that a hinge domain is a short sequence of amino acids that facilitates antibody flexibility (see, e.g., Woof et al., *Nat. Rev. Immunol.,* 4(2): 89-99 (2004)). The hinge domain may be positioned between the antigen recognition domain and the T-cell activation domain. The hinge domain may comprise any suitable sequence derived or obtained from any suitable molecule. Preferably, the hinge domain comprises a human sequence. In one embodiment, for example, the hinge domain is a portion of the human CD8α molecule or human CD28 molecule.

The CAR may comprise a TM domain. The TM domain can be any TM domain derived or obtained from any molecule known in the art. Preferably, the TM domain is a human TM domain. For example, the TM domain may comprise the TM domain of a human CD8α molecule or a human CD28 molecule. CD8 is a TM glycoprotein that serves as a co-receptor for the T-cell receptor (TCR), and is expressed primarily on the surface of cytotoxic T-cells. The most common form of CD8 exists as a dimer composed of a CD8α and CD8β chain. CD28 is expressed on T-cells and provides co-stimulatory signals required for T-cell activation. CD28 is the receptor for CD80 (B7.1) and CD86 (B7.2).

The CAR may comprise a T cell activation domain. The T cell activation domain may comprise an intracellular (i.e., cytoplasmic) T-cell signaling domain. The intracellular T-cell signaling domain can be obtained or derived from a CD28 molecule, a CD3 zeta (ζ) molecule, an Fc receptor gamma (FcRγ) chain, a CD27 molecule, an OX40 molecule, a 4-1BB molecule, an inducible T-cell costimulatory protein (ICOS), or other intracellular signaling molecules known in the art, or modified versions of any of the foregoing. As discussed above, CD28 is a T-cell marker important in T-cell co-stimulation. CD3ζ associates with TCRs to produce a signal and contains immunoreceptor tyrosine-based activation motifs (ITAMs). 4-1BB, also known as CD137, transmits a potent costimulatory signal to T-cells, promoting differentiation and enhancing long-term survival of T lymphocytes. ICOS is a CD28-superfamily costimulatory molecule that is expressed on activated T cells. In a preferred embodiment, the CD28, CD3 zeta, FcRγ, ICOS, 4-1BB, OX40, and CD27 are human.

The inventive CAR can comprise any one of aforementioned TM domains and any one or more of the aforementioned intracellular T-cell signaling domains in any combination. For example, the inventive CAR may comprise a CD8α TM domain and intracellular T-cell signaling domains of CD28 and CD3 zeta. Alternatively, for example, the inventive CAR may comprise a CD8α TM domain and intracellular T-cell signaling domains of CD3 zeta and 4-1BB. In still another example, the inventive CAR may comprise a CD8α TM domain and intracellular T-cell signaling domains of ICOS and CD3 zeta.

In one embodiment, the inventive CAR comprises, from the amino terminus to the carboxyl terminus, a human CD8α leader domain, a human anti-BCMA antibody heavy chain variable region, the hinge and transmembrane regions of the human CD8α molecule, the cytoplasmic T-cell signaling domain of the human CD28 molecule, and the cytoplasmic T-cell signaling domain of the human CD3ζ molecule. In another embodiment, the inventive CAR comprises, from the amino terminus to the carboxyl terminus, a human CD8α leader domain, a human anti-BCMA antibody heavy chain variable region, the hinge and transmembrane regions of the human CD8α molecule, the cytoplasmic T-cell signaling domain of the human 4-1BB molecule, and the cytoplasmic T-cell signaling domain of the human CD3ζ molecule. In still another embodiment, the inventive CAR comprises, from the amino terminus to the carboxyl terminus, a human CD8α leader domain, a human anti-BCMA antibody heavy chain variable region, the hinge and transmembrane regions of the human CD8α molecule, the cytoplasmic T-cell signaling domain of the human ICOS molecule, and the cytoplasmic T-cell signaling domain of the human CD3ζ molecule. Additional embodiments of the invention provide CARs comprising, consisting of, or consisting essentially of the amino acid sequence of any one of SEQ ID NOs: 17-28. The components of the CARs of SEQ ID NOs: 17-28 are set forth in Table A below.

TABLE A

| CAR (SEQ ID NO:) | Antigen Recognition Domain | TM Domain | T Cell Activation Domain |
|---|---|---|---|
| FHVH74-CD828Z (SEQ ID NO: 17) | SEQ ID NO: 13 | Human CD8α | Human CD28 Human CD3z |
| FHVH32-CD828Z (SEQ ID NO: 18) | SEQ ID NO: 14 | Human CD8α | Human CD28 Human CD3z |
| FHVH33-CD828Z (SEQ ID NO: 19) | SEQ ID NO: 15 | Human CD8α | Human CD28 Human CD3z |
| FHVH93-CD828Z (SEQ ID NO: 20) | SEQ ID NO: 16 | Human CD8α | Human CD28 Human CD3z |
| FHVH74-CD8BBZ (SEQ ID NO: 21) | SEQ ID NO: 13 | Human CD8α | Human 4-1BB Human CD3z |
| FHVH32-CD8BBZ (SEQ ID NO: 22) | SEQ ID NO: 14 | Human CD8α | Human 4-1BB Human CD3z |
| FHVH33-CD8BBZ (SEQ ID NO: 23) | SEQ ID NO: 15 | Human CD8α | Human 4-1BB Human CD3z |
| FHVH93-CD8BBZ (SEQ ID NO: 24) | SEQ ID NO: 16 | Human CD8α | Human 4-1BB Human CD3z |
| FHVH74-CD8ICOSZ (SEQ ID NO: 25) | SEQ ID NO: 13 | Human CD8α | Human ICOS Human CD3z |
| FHVH32-CD8ICOSZ (SEQ ID NO: 26) | SEQ ID NO: 14 | Human CD8α | Human ICOS Human CD3z |
| FHVH33-CD8ICOSZ (SEQ ID NO: 27) | SEQ ID NO: 15 | Human CD8α | Human ICOS Human CD3z |
| FHVH93-CD8ICOSZ (SEQ ID NO: 28) | SEQ ID NO: 16 | Human CD8α | Human ICOS Human CD3z |

In an embodiment of the invention, all domains of the CAR are human. In this regard, all of the leader domain, the hinge domain, the antigen recognition domain, the TM domain, and the T cell activation domain are human. Accordingly, the inventive CARs may, advantageously, have reduced anti-CAR immunogenicity, as described herein with respect to other aspects of the invention, as compared to CARs which include any one or more of a non-human leader domain, a non-human hinge domain, a non-human antigen recognition domain, a non-human TM domain, and a non-human T cell activation domain.

Included in the scope of the invention are functional portions of the inventive CARs described herein. The term "functional portion" when used in reference to a CAR refers to any part or fragment of the CAR of the invention, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the invention are functional variants of the inventive CARs described herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, about 50%, about 75%, about 80%, about 90%, about 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the inventive CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs of embodiments of the invention (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 1000 amino acids long, such as 50, 70, 75, 100, 125, 150, 175, 200, 300, 400, 500, 600, 700, 800, 900, 1000 or more amino acids in length.

The CARs of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, omithine, α-aminocyclopentane carboxylic acid, α-aminocyclohexane carboxylic acid, α-aminocycloheptane carboxylic acid, α-(2-amino-2-norbomane)-carboxylic acid, α,γ-diaminobutyric acid, α,β-diaminopropionic acid, homophenylalanine, and α-tert-butylglycine.

The CARs of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs of embodiments of the invention (including functional portions and functional variants thereof) can be obtained by methods known in the art. The CARs may be made by any suitable method of making polypeptides or proteins. For example, CARs can be recombinantly produced using the nucleic acids described herein using standard recombinant methods. See, for instance, Green and Sambrook, *Molecular Cloning: A Laboratory Manual*, 4<sup>th</sup> ed., Cold Spring Harbor Press, Cold Spring Harbor, NY 2012. Alternatively, the CARs described herein (including functional portions and functional variants thereof) can be commercially synthesized by companies, such as Synpep (Dublin, CA), Peptide Technologies Corp. (Gaithersburg, MD), and Multiple Peptide Systems (San Diego, CA). In this respect, the inventive CARs can be synthetic, recombinant, isolated, and/or purified.

Further provided by an embodiment of the invention is a nucleic acid comprising a nucleotide sequence encoding any of the CARs described herein (including functional portions and functional variants thereof). The nucleic acids of the invention may comprise a nucleotide sequence encoding any of the leader domains, hinge domains, antigen recognition domains, TM domains, and T cell activation domains described herein. In an embodiment of the invention, the nucleic acid may comprise, consist of, or consist essentially of the nucleotide sequence of any one of SEQ ID NO: 29 (FHVH74-CD828Z), SEQ ID NO: 30 (FHVH32-CD828Z), SEQ ID NO: 31 (FHVH33-CD828Z), SEQ ID NO: 32 (FHVH93-CD828Z), SEQ ID NO: 33 (FHVH74-CD8BBZ), SEQ ID NO: 34 (FHVH32-CD8BBZ), SEQ ID NO: 35 (FHVH33-CD8BBZ), SEQ ID NO: 36 (FHVH93-CD8BBZ), SEQ ID NO: 37 (FHVH74-CD8ICOSZ), SEQ ID NO: 38 (FHVH32-CD8ICOSZ), SEQ ID NO: 39 (FHVH33-CD8ICOSZ), and SEQ ID NO: 40 (FHVH93-CD8ICOSZ).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Green and Sambrook, supra. The nucleic acids can be constructed based on chemical synthesis and/or enzymatic ligation reactions using procedures known in the art. See, for example, Green and Sambrook, supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N<sup>6</sup>-isopentenyladenine, 1-methylguanine, 1-methylinosine, 2,2-dimethylguanine, 2-methyladenine, 2-methylguanine, 3-methylcytosine, 5-methylcytosine, N<sup>6</sup>-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxy-acetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-di-aminopurine. Alternatively, one or more of the nucleic acids of the invention can be purchased from companies, such as Macromolecular Resources (Fort Collins, CO) and Synthegen (Houston, TX).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, MD), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). The recombinant expression vector may be a viral vector, e.g., a retroviral vector (e.g., a gammaretroviral vector) or a lentiviral vector.

In an embodiment, the recombinant expression vectors of the invention can be prepared using standard recombinant DNA techniques described in, for example, Sambrook and Green, supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning. In addition to the inventive nucleic acid sequence encoding the CAR, the recombinant expression vector preferably comprises expression control sequences, such as promoters, enhancers, polyadenylation signals, transcription terminators, internal ribosome entry sites (IRES), and the like, that provide for the expression of the nucleic acid sequence in a host cell.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine daminase, purine nucleoside phosphorylase, and nitroreductase.

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5αE. coli cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant CAR, the host cell may be a mammalian cell. The host cell may be a human cell. The host cell can be of any cell type, can originate from any type of tissue, and can be of any developmental stage. The host cell may be a peripheral blood lymphocyte (PBL) or a peripheral blood mononuclear cell (PBMC).

In an embodiment of the invention, the host cell is a T cell. For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD8$^+$ T cells (e.g., cytotoxic T cells), tumor infiltrating cells, memory T cells, naïve T cells, and the like. The T cell may be a CD8$^+$ T cell or a CD4$^+$ T cell.

In an embodiment of the invention, the host cell is a natural killer (NK) cell. NK cells are a type of cytotoxic lymphocyte that plays a role in the innate immune system. NK cells are defined as large granular lymphocytes and constitute the third kind of cells differentiated from the common lymphoid progenitor which also gives rise to B and T lymphocytes (see, e.g., *Immunobiology,* 9$^{th}$ ed., Janeway et al., eds., Garland Publishing, New York, NY (2016)). NK cells differentiate and mature in the bone marrow, lymph node, spleen, tonsils, and thymus. Following maturation, NK cells enter into the circulation as large lymphocytes with distinctive cytotoxic granules. NK cells are able to recognize and kill some abnormal cells, such as, for example, some tumor cells and virus-infected cells, and are thought to be important in the innate immune defense against intracellular pathogens. As described above with respect to T-cells, the NK cell can be any NK cell, such as a cultured NK cell, e.g., a primary NK cell, or an NK cell from a cultured NK cell line, or an NK cell obtained from a mammal. If obtained from a mammal, the NK cell can be obtained from numerous sources, including but not limited to blood, bone marrow, lymph node, the thymus, or other tissues or fluids. NK cells can also be enriched for or purified. The NK cell preferably is a human NK cell (e.g., isolated from a human). NK cell lines are available from, e.g., the American Type Culture Collection (ATCC, Manassas, VA) and include, for example, NK-92 cells (ATCC CRL-2407), NK92MI cells (ATCC CRL-2408), and derivatives thereof.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The inventive recombinant expression vectors encoding a CAR may be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation; DEAE-dextran; electroporation; cationic liposome-mediated transfection; tungsten particle-facilitated microparticle bombardment; and strontium phosphate DNA co-precipitation. Phage or viral vectors can be introduced into host cells, after growth of infectious particles in suitable packaging cells, many of which are commercially available.

Included in the scope of the invention are conjugates, e.g., bioconjugates, comprising any of the inventive CARs (including any of the functional portions or variants thereof), nucleic acids, recombinant expression vectors, host cells, or populations of host cells. Conjugates, as well as methods of synthesizing conjugates in general, are known in the art.

CARs (including functional portions and variants thereof), nucleic acids, recombinant expression vectors, and host cells (including populations thereof), all of which are collectively referred to as "inventive CAR materials" hereinafter, can be isolated and/or purified. The term "isolated" as used herein means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

The inventive CAR materials can be formulated into a composition, such as a pharmaceutical composition. In this regard, an embodiment of the invention provides a pharmaceutical composition comprising any of the CARs, functional portions, functional variants, nucleic acids, expression vectors, or host cells (including populations thereof), and a pharmaceutically acceptable carrier. The inventive pharmaceutical compositions containing any of the inventive CAR materials can comprise more than one inventive CAR material, e.g., a CAR and a nucleic acid, or two or more different CARs. Alternatively, the pharmaceutical composition can comprise an inventive CAR material in combination with other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises the inventive host cell or populations thereof.

Preferably, the carrier is a pharmaceutically acceptable carrier. With respect to pharmaceutical compositions, the carrier can be any of those conventionally used for the particular inventive CAR material under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive CAR material, as well as by the particular method used to administer the inventive CAR material. In a preferred embodiment, the CAR is expressed by a host cell, which is preferably a T cell or an NK cell, and host cells expressing the CAR are administered to a patient. These cells could be autologous or allogeneic in relation to the recipient of the cells. A nucleic acid encoding the CAR may be introduced to the cells by any of a variety of methods of genetic modification including, but not limited to, transduction with a gamma-retrovirus, a lentivirus, or a transposon system. There are a variety of suitable formulations of the pharmaceutical composition of the invention. Suitable formulations may include any of those forparenteral, subcutaneous, intravenous, intramuscular, intratumoral, intraarterial, intrathecal, or interperitoneal administration. More than one route can be used to administer the inventive CAR materials, and in certain instances, a particular route can provide a more immediate and more effective response than another route.

Preferably, the inventive CAR material is administered by injection, e.g., intravenously. When the inventive CAR material is a host cell expressing the inventive CAR (or functional variant thereof), the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumen.

The composition can employ time-released, delayed release, and sustained release delivery systems such that the delivery of the inventive composition occurs prior to, and with sufficient time to cause, sensitization of the site to be treated. Many types of release delivery systems are available and known to those of ordinary skill in the art. Such systems can avoid repeated administrations of the composition, thereby increasing convenience to the subject and the physician, and may be particularly suitable for certain composition embodiments of the invention.

Without being bound to a particular theory or mechanism, it is believed that by eliciting an antigen-specific response against BCMA, the inventive CARs provide for one or more of the following: targeting and destroying BCMA-expressing cancer cells, reducing or eliminating cancer cells, facilitating infiltration of immune cells to tumor site(s), and enhancing/extending anti-cancer responses.

It is contemplated that the inventive CARs materials can be used in methods of treating or preventing a disease, e.g., cancer, in a mammal. Without being bound to a particular theory or mechanism, the inventive CARs have biological activity, e.g., ability to recognize antigen, e.g., BCMA, such that the CAR when expressed by a cell is able to mediate an immune response against the cell expressing the antigen, e.g., BCMA, for which the CAR is specific. In this regard, an embodiment of the invention provides a method of treating or preventing cancer in a mammal, comprising administering to the mammal any of the CARs, the nucleic acids, the recombinant expression vectors, the host cells, the population of cells, and/or the pharmaceutical compositions of the invention in an amount effective to treat or prevent cancer in the mammal. In a preferred embodiment, the method comprises infusing the mammal with host cells transduced with the inventive CAR.

One or more isolated host cells expressing the inventive BCMA CAR described herein can be contacted with a population of cancer cells that express BCMA ex vivo, in vivo, or in vitro. "Ex vivo" refers to methods conducted within or on cells or tissue in an artificial environment outside an organism with minimum alteration of natural conditions. In contrast, the term "in vivo" refers to a method that is conducted within living organisms in their normal, intact state, while an "in vitro" method is conducted using components of an organism that have been isolated from its usual biological context. The inventive method preferably involves ex vivo and in vivo components. In this regard, for example, the isolated host cells described above can be cultured ex vivo under conditions to express the inventive anti-BCMA CAR, and then directly transferred into a mammal (preferably a human) affected by a BCMA-positive cancer, e.g., multiple myeloma. Such a cell transfer method is referred to in the art as "adoptive cell transfer (ACT)," in which immune-derived cells are transferred into a recipient to transfer the functionality of the immune-derived cells to the host. The immune-derived cells may have originated from the recipient or from another individual. Adoptive cell transfer methods to treat various types of cancers, including hematological cancers such as myeloma.

Once the composition comprising host cells expressing the inventive CAR-encoding nucleic acid sequence, or a vector comprising the inventive CAR-encoding nucleic acid sequence, is administered to a mammal (e.g., a human), the biological activity of the CAR can be measured by any suitable method known in the art. In accordance with the inventive method, the CAR binds to BCMA on the cancer, and the cancer cells are destroyed. Binding of the CAR to BCMA on the surface of cancer cells can be assayed using any suitable method known in the art, including, for example, ELISA (enzyme-linked immunosorbent assay) and flow cytometry. The ability of the CAR to destroy cells can be measured using any suitable method known in the art, such as cytotoxicity assays described in, for example, Kochenderfer et al., *J. Immunotherapy,* 32(7): 689-702 (2009), and Herman et al. *J. Immunological Methods,* 285 (1): 25-40 (2004). The biological activity of the CAR also can be measured by assaying expression of certain cytokines, such as CD107a, IFNγ, IL-2, and TNF.

An embodiment of the invention further comprises lymphodepleting the mammal prior to administering the inventive CAR material. Examples of lymphodepletion include, but may not be limited to, nonmyeloablative lymphodepleting chemotherapy, myeloablative lymphodepleting chemotherapy, total body irradiation, etc.

For purposes of the inventive methods, wherein host cells or populations of cells are administered, the cells can be cells that are allogeneic or autologous to the mammal. Preferably, the cells are autologous to the mammal.

An "effective amount" or "an amount effective to treat" refers to a dose that is adequate to prevent or treat cancer in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the particular CAR material selected, method of administration, timing and frequency of administration, the existence, nature, and extent of any adverse side-effects that might accompany the administration of a particular CAR material, and the desired physiological effect. It will be appreciated by one of skill in the art that various diseases or disorders (e.g., cancer) could require prolonged treatment involving multiple administrations, perhaps using the inventive CAR materials in each or various rounds of administration. By way of example and not intending to limit the invention, the dose of the inventive CAR material can be about 0.001 to about 1000 mg/kg body weight of the subject being treated/day, from about 0.01 to about 10 mg/kg body weight/day, about 0.01 mg to about 1 mg/kg body weight/day. In an embodiment of the invention, the dose may be from about $1\times10^4$ to about $1\times10^{10}$ cells expressing the inventive CAR per kg body weight. When the inventive CAR material is a host cell, an exemplary dose of host cells may be a minimum of one million cells (1 mg cells/dose), e.g., $1\times10^9$ cells per kg body weight. When the inventive CAR material is a nucleic acid packaged in a virus, an exemplary dose of virus may be 1 ng/dose.

For purposes of the invention, the amount or dose of the inventive CAR material administered should be sufficient to effect a therapeutic or prophylactic response in the subject or animal over a reasonable time frame. For example, the dose of the inventive CAR material should be sufficient to bind to antigen, or detect, treat or prevent disease, e.g., cancer, in a period of from about 2 hours or longer, e.g., about 12 to about 24 or more hours, from the time of administration. In certain embodiments, the time period could be even longer.

The dose will be determined by the efficacy of the particular inventive CAR material and the condition of the animal (e.g., human), as well as the body weight of the animal (e.g., human) to be treated.

For purposes of the invention, an assay, which comprises, for example, comparing the extent to which target cells are lysed and/or IFN-γ is secreted by T cells expressing the inventive CAR upon administration of a given dose of such T cells to a mammal, among a set of mammals of which is each given a different dose of the T cells, could be used to determine a starting dose to be administered to a mammal. The extent to which target cells are lysed and/or IFN-γ is secreted upon administration of a certain dose can be assayed by methods known in the art.

When the inventive CAR materials are administered with one or more additional therapeutic agents, one or more additional therapeutic agents can be coadministered to the mammal. By "coadministering" is meant administering one or more additional therapeutic agents and the inventive CAR materials sufficiently close in time such that the inventive CAR materials can enhance the effect of one or more additional therapeutic agents, or vice versa. In this regard, the inventive CAR materials can be administered first and the one or more additional therapeutic agents can be administered second, or vice versa. Alternatively, the inventive CAR materials and the one or more additional therapeutic agents can be administered simultaneously. An exemplary therapeutic agent that can be co-administered with the CAR materials is IL-2. It is believed that IL-2 enhances the therapeutic effect of the inventive CAR materials. Without being bound by a particular theory or mechanism, it is believed that IL-2 enhances therapy by enhancing the in vivo expansion of the numbers of cells expressing the inventive CARs.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the inventive methods, the cancer can be any cancer. In an embodiment of the invention, the cancer is a BCMA-expressing cancer. In an embodiment of the invention, the cancer is multiple myeloma or Hodgkin's lymphoma.

As discussed herein, multiple myeloma, also known as plasma cell myeloma or Kahler's disease, is a cancer of plasma cells, which are a type of white blood cell normally responsible for the production of antibodies (Raab et al., *Lancet,* 374: 324-329 (2009)). Multiple myeloma affects 1-4 per 100,000 people per year. The disease is more common in men, and for yet unknown reasons is twice as common in African Americans as it is in Caucasian Americans. Multiple myeloma is the least common hematological malignancy (14%) and constitutes 1% of all cancers (Raab et al., supra). Treatment of multiple myeloma typically involves high-dose chemotherapy followed by hematopoietic stem cell transplanatation (allogenic or autologous); however, a high rate of relapse is common in multiple myeloma patients that have undergone such treatement. As discussed above, BCMA is highly expressed by multiple myeloma cells (see, e.g., Novak et al., supra; Neri et al., supra; Bellucci et al., supra; and Moreaux et al., supra).

Hodgkin's lymphoma (formerly known as Hodgkin's disease) is a cancer of the immune system that is marked by the presence of a multinucleated cell type called Reed-Sternberg cells. The two major types of Hodgkin's lymphoma include classical Hodgkin's lymphoma and nodular lymphocyte-predominant Hodgkin's lymphoma. Hodgkin's lymphoma currently is treated with radiation therapy, chemotherapy, or hematopoietic stem cell transplantation, with the choice of treatment depending on the age and sex of the patient and the stage, bulk, and histological subtype of the disease. BCMA expression has been detected on the surface of Hodgkin's lymphoma cells (see, e.g., Chiu et al., *Blood,* 109(2): 729-739 (2007)).

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, e.g., cancer, or a symptom or condition thereof.

Another embodiment of the invention provides any of the CARs, nucleic acids, recombinant expression vectors, host cells, populations of cells, and/or pharmaceutical compositions described herein with respect to other aspects of the invention for use in a method of treating or preventing cancer in a mammal. Still another embodiment of the invention provides the use of any of the CARs, nucleic acids, recombinant expression vectors, host cells, populations of cells, and/or pharmaceutical compositions described herein with respect to other aspects of the invention in the manufacture of a medicament for the treatment or prevention of cancer in a mammal. The cancer may be any of the cancers described herein.

The following examples further illustrate the invention but, of course, should not be construed as in any way limiting its scope.

EXAMPLES

The materials and methods employed in Examples 1-10 are provided below.

Cell Lines and Primary Cells

Multiple myeloma BCMA⁺ cell lines H929, U266, and RPMI8226 were obtained from ATCC. BCMA-negative lung cancer cell line A549 was obtained from ATCC. BCMA-negative sarcoma cell line was obtained from ATCC.

BCMA-K562 and K562 cells from ATCC were transduced with the gene for full-length BCMA in the laboratory prior to the following experiments. NGFR-K562 and K562 cells were transduced with the gene for low-affinity nerve growth factor in the laboratory prior to the following experiments. The same gammaretroviral vector and methods were used to transduce BCMA-K562 and NGFR-K562 cells.

Tissue samples or peripheral blood mononuclear cells (PMBC) from six patients with multiple myeloma were designated as Myeloma Patients 1-6. PBMC was used from 3 subjects with melanoma and the donors were labeled as Donor A, Donor B, and Donor C. Primary CD34⁺ hematopoietic cells from three healthy donors were also obtained. All of the human samples used were obtained from patients enrolled on Institutional Review Board approved clinical trials at the National Cancer Institute.

Constructing Fully-Human Human-Chain-Only (FHVH) CARs

A series of CARs that contained fully human heavy-chain-only antigen-recognition (FHVH) domains were prepared. The sequence of each CAR followed this pattern from the 5' end to the 3' end: CD8α leader sequence, one of 4 single heavy chain variable region domains, and hinge and transmembrane regions of the human CD8α molecule. Then, the cytoplasmic portion of either the CD28, 4-1BB, or the inducible T-cell costimulatory (ICOS) molecules were added, followed by the cytoplasmic portion of the CD3ζ molecule. The full amino acid sequences of these CARS are provided in SEQ ID Nos: 17-28.

The four fully-human heavy-chain-only CAR antigen-recognition domains were designated FHVH 74, 32, 33, and 93, as shown in FIGS. 1A-1L. The CAR names also include the CD8α hinge and transmembrane domain, the costimulatory domain included, and the CD3ζ domain. For example, FHVH74-CD828Z has the FHVH74 antigen-recognition domain, a hinge and transmembrane domain from CD8α, a CD28 costimulatory domain, and the CD3ζ T-cell activation domain. 11D5-3-CD828Z anti-BCMA CAR was used as a positive control.

These CARs were constructed and the CAR nucleotide sequences were ligated into the MSGV gammaretroviral vector backbone by standard methods. The full nucleotide sequences of the CARs are provided in SEQ ID Nos: 29-40. BCMA-specific variable heavy chain sequences were synthesized as GBLOCK fragments (Integrated DNA Technologies (IDT), Skokie, IL). Each synthesized fragment contained a GTC trinucleotide, the Ncol site, the CD8α leader sequence, the FHVH sequence, part of the CD8α hinge and transmembrane domain, the Blpl site, and a TATCGT hexanucleotide (provided as SEQ ID No. 41). The GTC and TATCGT (SEQ ID NO: 41) nucleotides were added to ensure complete end cleavage with Ncol and Blpl. Fragments were digested with Blpl and NCOI-HF (New England Biolabs, Ipswich, MA) for two hours at 37° C. Digested fragments were then purified using the QIAQUICK PCR purification kit (Qiagen). Fragments were ligated into the Blpl/Ncol-HF digested and gel-purified MSGV vector backbones that also included other components of the CAR not included in the GBLOCK (Integrated DNA Technologies (IDT), Skokie, IL) fragments.

The CAR components included in the MSGV vector backbones were: the remainder of CD8α domain that was not included in the GBLOCK (Integrated DNA Technologies (IDT), Skokie, IL) fragment, the sequence encoding the costimulatory domain, either CD28 or 4-1BB or ICOS, and the CD3ζ domain. The ligation of each GBLOCK (Integrated DNA Technologies (IDT), Skokie, IL) CAR fragment and the MSGV vector backbone fragment was carried out by using the Rapid DNA Ligation Kit (Roche Applied Sciences).

CAR Detection on T Cells

T cells that were transduced with one of the CAR vectors and untransduced T cells were washed and stained with a BCMA-Fc protein labeled with phycoerythrin to detect cell-surface CAR molecules. Five hundred thousand T cells were suspended in 50 mL of staining buffer, and a titered amount of BCMA-Fc-PE reagent was added. Staining for CD3, CD4, and CD8 was also performed by using standard methods. Dead cells were excluded by using 7-AAD (7-amino-acinomycin dye, (BD Biosciences)).

T Cell Culture

PBMC were thawed and washed in T cell medium that contained AIM V medium (Invitrogen, Waltham, MA) plus 5% AB serum (Valley Biomedical, Winchester, VA), 100 U/mL penicillin, and 100 ng/mL streptomycin. Prior to transductions, PBMC were suspended at a concentration of $1 \times 10^6$ cells/mL in T cell medium plus 50 ng/mL of the anti-CD3 monoclonal antibody OKT3 (Ortho, Bridgewater, NJ), and 300 IU/mL of IL-2. After transductions, T cells were maintained in T-cell medium plus IL-2.

Gammaretroviral Transductions

To produce replication-incompetent gammaretroviruses, packaging cells were transfected with plasmids encoding CARs along with a plasmid encoding the RD114 envelope protein. Gammaretroviral transduction of T cells was performed 2 days after initiation of T-cell cultures.

Interferon-γ and Tumor Necrosis Factor Alpha ELISAs

One-hundred thousand BCMA⁺ or BCMA-negative target cells were combined with 100,000 CAR-transduced T cells in duplicate wells of a 96 well round bottom plate in 200 µL of AIM-V medium+5% human serum. The plates were incubated at 37° C. for 18-20 hours. Following the incubation, ELISAs for interferon gamma (INFγ) were performed using standard methods (Pierce). Tumor necrosis factor alpha (TNF) ELISAs were performed using standard methods (R&D).

CD107a Assay

For each T cell culture that was tested, two tubes were prepared. One tube contained BCMA-K562 cells and the other tube contained NGFR-K562 cells. Both tubes contained CAR-transduced T cells, 1 ml of AIM-V medium+5% human AB serum, a titrated concentration of an anti-CD107a antibody (eBioscience, clone eBioH4A3) and 1 µL of GOLGI STOP (monesin, BD Biosciences, San Jose, CA). All tubes were incubated at 37° C. for 4 hours and then stained for CD3, CD4, and CD8.

Flow Cytometry

For anti-BCMA staining, cells were stained with polyclonal biotin-labeled goat-ant-human BCMA antibodies (R&D Systems, catalog number BAF 193) followed by streptavidin (BD). Bone marrow cells were also stained with anti-CD38 (eBioscience). Bone marrow cells were also stained with anti-CD38 (eBioscience) and anti-CD56 (BD). Flow cytometry analysis for all experiments was performed using a FLOWJO software (Tree Star, Inc. Oregon, US).

Proliferation Assays

Cocultures were set up in 24-well plates. Target cells included in cocultures were either $0.5 \times 10^6$ irradiated BCMA-K562 cells or $0.5 \times 10^6$ irradiated NGFR-K562 cells. The cocultures also included $1 \times 10^6$ T cells from cultures that had been transduced with either anti-bcma2 or SP6. The T cells were labeled with carboxyfluorescein diacetate succinimidyl ester (CFSE, Invitrogen) as previously described. The medium used in the cocultures was AIM V+5% human AB serum. IL-2 was not added to the medium. Four days after initiation, the live cells in each coculture were counted with trypan blue for dead cell exclusion, and flow cytometry was performed

Cytotoxicity Assay

Cytotoxicity was measured by comparing survival of BCMA⁺ target cells relative to the survival of negative-control CCRF-CEM cells. Both of these cell types were combined in the same tubes with CAR-transduced T cells. CCRF-CEM negative control cells were labeled with the fluorescent dye 5-(and-6)-(((4-chloromethyl)benzoyl) amino) tetramethylrhodamine (CMTMR) (Invitrogen), and BCMA⁺ target cells were labeled with CFSE. Cocultures were set up in sterile 5 mL test tubes (BD) in duplicate at multiple T cell to target cell ratios. The target cells contained in the tubes were 50,000 BCMA⁺ target cells along with 50,000 CCRF-CEM negative-control cells. The cultures were incubated for 4 hours at 37° C. Immediately after the incubation, 7AAD (7-amino-actinomycin D) (BD) was added, and flow cytometry acquisition was performed. For each T cell plus target-cell culture, the percent survival of BCMA⁺ target cells was determined by dividing the percent live BCMA⁺ cells by the percent live CCRF-CEM negative control cells. The corrected percent survival of BCMA⁺ target cells was calculated by dividing the percent survival of BCMA⁺ target cells in each T cell plus target cell culture by the ratio of the percent live BCMA⁺ target cells to percent live CCRF-CEM negative-control cells in tubes containing only BCMA⁺ target cells and CCRF-CEM cells without effector T cells. This correction was necessary to account for variation in the starting cell numbers and for spontaneous target cell death. Cytotoxicity was calculated as follows: the percent cytotoxicity of BCMA⁺ target cells=100-corrected percent survival of BCMA⁺ target cells.

In Vivo Murine Model Treatment Experiments

NSG mice (NOD.Cg-Prkdc$^{scid}$ Il2rg$^{tm1\,Wjl}$/SzJ) from The Jackson Laboratory were used. Mice received intradermal injections of RPMI8226 cells. Tumors were allowed to grow for 10 days. Then the mice received intravenous infusions of the doses noted in Example 9 (FIGS. 9B-9C) or Example 10 of human T cells that were transduced with CARs indicated in Example 9 (FIGS. 9B-9C), Example 10, or left untransduced. Tumors were measured with calipers every 3 days. The longest length and the length perpendicular to the longest length were multiplied to obtain the tumor size (area) in mm². When the longest length reached 15 mm, mice were sacrificed. Animal studies were approved by the National Cancer Institute Animal Care and Use Committee.

Example 1

This example demonstrates the design of CARs with heavy-chain-only antigen recognition domains.

Twelve CARs with fully-human heavy-chain-only antigen recognition domains were designed, as shown in FIGS. 1A-1L. The general design of these CARs from the N-terminus to the C-terminus comprises: the CD8a leader sequence, a fully-human heavy chain variable region, the CD8a hinge and transmembrane domains, the cytoplasmic portion of one of 3 costimulatory domains, the cytoplasmic portion of the CD3ζ activation domain. The 3 costimulatory domains tested were CD28, 4-1BB, and inducible T cell costimulatory (ICOS). This example demonstrates the first CARs to be reported with heavy-chain-only antigen recognition domains.

Example 2

This example demonstrates that heavy-chain-only CARs were expressed on the surface of T cells.

To conduct the experiments, primary human T cells from multiple myeloma (MM) patients were transduced with the heavy-chain-only CARs shown in FIG. 2. CAR surface expression was evaluated by staining the cells with a BCMA-Fc reagent followed by flow cytometry (FIG. 2). All four FHVH CARs were consistently expressed on the surface of T cells as shown in FIG. 2. The median fluorescence intensity of staining was somewhat higher for the 11D5-3-CD828Z control CAR that contained both a light chain variable region and heavy chain variable regions for unknown reasons.

Example 3

This example demonstrates that heavy-chain-only CARs degranulated in a BCMA-specific manner.

BCMA-specific degranulation of T cells expressing each of the four FHVH CARs shown in FIG. 3 and the 11D5-3-CD828Z CAR were measured. T cells transduced with each of the FHVH CARs upregulated CD107a specifically in response to stimulation with BCMA-expressing target cells but not BCMA-negative target cells as shown in FIG. 3. T cells expressing 11D5-3 also upregulated CD107a (FIG. 3). Upregulation of CD107a demonstrates BCMA-specific degranulation of the T cells, which is part of the perforin-mediated cytotoxicity process.

Example 4

This example demonstrates that T cells expressing heavy-chain-only CARs released cytokines in a BCMA-specific manner.

Primary human T cells from MM patients were evaluated for their ability to release interferon gamma (IFN$\gamma$) and tumor necrosis factor alpha (TNF) when cultured in vitro with a variety of target cell lines. All FHVH CARs shown in Tables 1-3 were found to release these cytokines in a highly BCMA-specific manner, as set forth in Tables 1-3, respectively.

TABLE 1

| | | | | | | | |
|---|---|---|---|---|---|---|---|
| | | Interferon-gamma ELISA | | | | | |
| | BCMA-K562 | RPMI-8226 | NGFR-K562 | CCRF-CEM | 293GP | T-cells Only | % CAR+ |
| Untransduced | 39.1 | 44.4 | 37.7 | 17.0 | 17.0 | 16.0 | 0.6 |
| 11D5-3-CD828Z | 36260.4 | 1598.7 | 57.1 | 28.6 | 20.0 | 21.8 | 68.4 |
| FHVH74-CD828Z | 35717.6 | 2683.3 | 52.3 | 21.0 | 17.8 | 15.5 | 61.3 |
| FHVH32-CD828Z | 37876.2 | 3060.9 | 66.9 | 29.4 | 17.3 | 16.4 | 55.7 |
| FHVH33-CD828Z | 31323.4 | 4059.5 | 78.3 | 17.5 | 18.5 | 15.4 | 60.5 |
| FHVH93-CD828Z | 31288.2 | 3786.0 | 48.9 | 20.6 | 14.7 | 15.9 | 52.2 |

With reference to Table 1, cultured T cells were transduced with the indicated CARs and cultured overnight with the indicated target cells (top row). After the overnight incubation, a standard ELISA assay was performed on the culture supernatant. BCMA-K562 and RPMI8226 are BCMA+. NGFR-K562, CCRF-CEM, and 293GP are BCMA-negative. The percentage of T cells expressing the indicated CAR was determined by staining with a BCMA-Fc-PE reagent followed by flow cytometry. The % CAR+ equals the percentage of CD3+ cells transduced with each CAR that stained with the BCMA-Fc-PE reagent minus the percentage of untransduced CD3+ lymphocytes that stained with the BCMA-Fc-PE reagent. Except for the % CAR+ column, all numbers are pg/mL of interferon-gamma.

TABLE 2

| | | | | | | | |
|---|---|---|---|---|---|---|---|
| | | Tumor-necrosis factor-alpha ELISA | | | | | |
| | BCMA-K562 | RPMI-8226 | NGFR-K562 | CCRF-CEM | 293GP | T-cells Only | % CAR+ |
| Untransduced | 8.8 | 6.1 | 8.2 | 5.7 | 8.1 | 6.1 | 0.6 |
| 11D5-3-CD828Z | 2219.2 | 67.6 | 10.2 | 7.7 | 7.1 | 6.4 | 68.4 |
| FHVH74-CD828Z | 2344.1 | 107.8 | 9.3 | 6.6 | 9.1 | 6.1 | 61.3 |
| FHVH32-CD828Z | 2261.6 | 113.8 | 9.9 | 7.0 | 9.5 | 6.8 | 55.7 |
| FHVH33-CD828Z | 2161.9 | 209.9 | 10.4 | 6.4 | 10.2 | 5.7 | 60.5 |
| FHVH93-CD828Z | 1868.2 | 200.9 | 10.0 | 7.1 | 8.4 | 6.2 | 52.2 |

With reference to Table 2, cultured T cells were transduced with the indicated CARs and cultured overnight with the indicated target cells (top row). After the overnight incubation, a standard ELISA assay was performed on the culture supernatant. BCMA-K562 is BCMA⁺. All other targets are BCMA-negative. The percentage of T cells expressing the indicated CAR was determined by staining with a BCMA-Fc-PE reagent followed by flow cytometry. The % CAR⁺ equals the percentage of CD3⁺ cells transduced with each CAR that stained with the BCMA-Fc-PE reagent minus the percentage of untransduced CD3⁺ lymphocytes that stained with the BCMA-Fc-PE reagent. Except for the % CAR⁺ column, all numbers are pg/mL of interferon-gamma.

The results of Tables 1 and 2 show that the indicted CARs specifically recognize BCMA⁺ target cells.

The ability of FHVH CAR T cells to kill BCMA+ target cells was assessed. It was shown that FHVH33-CD828Z and FHVH33-CD8BBZ have the ability to kill BCMA+ RPMI226 cells as compared to UT cells, as shown in FIGS. 5A and 5B.

Example 7

This example demonstrates that heavy-chain-only CARs with a 4-1BB costimulatory domain are expressed and functional.

The four fully-human heavy-chain-only CARs shown in FIG. 6, with 4-1BB costimulatory domains were constructed and assessed. All four of these CARs were expressed on the surface of primary human T cells, but FHVH33-CD8BBZ consistently had the highest expression (FIG. 6) and was

TABLE 3

| | Recognition of BCMA⁺ target cells | | | | | | | |
| | BCMA-K562 | A549 | TC71 | MDA-231 | COLO | HEPG2 | 293GP | T-cells Only | % CAR+ |
|---|---|---|---|---|---|---|---|---|---|
| Untransduced | 115.1 | 116.7 | 65.1 | 118.8 | 32.7 | 46.9 | 79.0 | 91.2 | 0.073 |
| FHVH74-CD828Z | 42485.2 | 103.2 | 123.1 | 120.3 | 16.7 | 52.7 | 43.1 | 49.5 | 45.7 |
| FHVH33-CD828Z | 26994.1 | 223.2 | 181.2 | 407.6 | 45.2 | 109.2 | 81.8 | 94.4 | 32.2 |

With reference to Table 3, cultured T cells were transduced with the indicated CARs and cultured overnight with the indicated target cells (top row). After the overnight incubation, a standard ELISA assay was performed on the culture supernatant. BCMA-K562 is BCMA⁺. All other targets are BCMA-negative. The percentage of T cells expressing the indicated CAR was determined by staining with a BCMA-Fc-PE reagent followed by flow cytometry. The % CAR⁺ equals the percentage of CD3⁺ cells transduced with each CAR that stained with the BCMA-Fc-PE reagent minus the percentage of untransduced CD3⁺ lymphocytes that stained with the BCMA-Fc-PE reagent. Except for the % CAR⁺ column, all numbers are pg/mL of interferon-gamma.

The results in Table 3 show that T cells expressing FHVH-CD828Z or FHVH-CD828Z specifically recognize BCMA⁺ target cells.

Example 5

This example demonstrates that T cells expressing heavy-chain-only CARs proliferated in a BCMA-specific manner in vitro.

CFSE-labeled CAR-expressing primary T cells from MM patients were cultured with irradiated BCMA⁺ or BCMA-negative target cells. All four FHVH CARs shown in FIGS. 4B-4E proliferated in a BCMA-specific manner as shown in FIGS. 4B-4E. T cells expressing the 11D5-3-CD828Z CAR also proliferated in a BCMA-specific manner (FIG. 4A). In addition to documenting BCMA-specific proliferation by dilution of CFSE, BCMA-specific proliferation was also demonstrated by an increase in the absolute number of CAR-expressing T cells that were cultured with BCMA⁺ target cells. The absolute number of CAR P T cells increased when the T cells were cultured with BCMA⁺ target cells as shown in FIG. 4F.

Example 6

This example demonstrates that T cells expressing heavy-chain-only CARs kill BCMA⁺ target cells.

therefore selected for further study. Results from a functional assessment of FHVH33-CD8BBZ are shown in FIGS. 7A-7F. These CAR-expressing T cells produced IFNγ and degranulated in a BCMA-specific manner.

Example 8

This example demonstrates that anti-BCMA CAR-transduced T cells recognize primary multiple myeloma cells.

T cells that were either untransduced or which expressed the FHVH33-CD828Z or FHVH33-CD8BBZ CAR were incubated with autologous bone marrow myeloma cells (90% purity) for 4 hours. Upregulation of CD107a was measured as a marker of T-cell degranulation, and co-expression of CD8 or CD4 was also measured. The percentages of cells with the indicated phenotypes are shown in Table 4. As shown in Table 4, T cells transduced with FHVH33-CD828Z or FHVH33-CD8BBZ CAR upregulated CD107a expression following co-culture with target bone marrow myeloma cells.

TABLE 4

| | Untransduced | FHVH33-CD828Z | FHVH33-CD8BBZ |
|---|---|---|---|
| CD107a+/CD4+ | 2.3 | 13.0 | 50.7 |
| CD107a−/CD4− | 0.0 | 0.0 | 0.0 |
| CD107a+/CD4− | 0.0 | 0.0 | 0.0 |
| CD107a−/CD4+ | 97.7 | 87.0 | 49.3 |
| CD107a+/CD8+ | 4.8 | 27.6 | 40.0 |
| CD107a−/CD8− | 0.0 | 0.0 | 0.0 |
| CD107a+/CD8− | 0.0 | 0.0 | 0.0 |
| CD107a−/CD8+ | 95.2 | 72.4 | 60.0 |

T cells that were either untransduced (UT) or which expressed the FHVH33-CD828Z or FHVH33-CD8BBZ CAR were incubated with autologous bone marrow myeloma cells (90% purity) or control PBMC overnight. Interferon-gamma release was measured with a standard ELISA assay. The results are shown in FIG. 8. As shown in FIG. 8, cells transduced with FHVH33-CD828Z or FHVH33-CD8BBZ CAR secreted IFN-γ following co-culture with target bone marrow myeloma cells.

Example 9

This example demonstrates a dose titration of FHVH33-CD8BBZ-expressing T cells in mice.

As shown in FIG. 9A, NSG mice were injected intradermally with RPMI8226 cells. Tumors were allowed to grow for 10 days. On day 0, the mice received intravenous infusions of the indicated number of FHVH33-CD8BBZ-expressing T cells. Mice received one of three different doses of FHVH33-CD8BBZ CART cells, and another group of mice was left untreated. The mice all had established tumors at the time of T-cell infusion.

As shown in FIG. 9B, $2.2 \times 10^6$ FHVH33-CD8BBZ T cells were able to eradicate tumors from all mice, and the effectiveness of the FHVH33-CD8BBZ CART cells decreased in a dose-dependent manner. All mice left untreated had progressive enlargement of their tumors. (n=5 mice per group).

The survival of the mice is shown in FIG. 9C. All mice receiving $2.2 \times 10^6$ FHVH33-CD8BBZ-expressing T cells survived and were healthy for the duration of the experiment.

Example 10

This example demonstrates the eradication of BCMA+ tumors in NSG mice.

Mice were injected intradermally with RPMI8226 cells. Tumors were allowed to grow for 10 days. On day 0, the mice received intravenous infusions of $1 \times 10^6$ T cells expressing the SP6-CD828Z, 11D5-3-CD8BBZ, FHVH33-CD8BBZ, or FHVH33-CD828Z CAR or mice were left untreated.

As shown in FIG. 10A, mice receiving infusions of T cells expressing the negative-control SP6-CD828Z CAR and untreated mice had progressive tumor growth. Mice receiving T cells expressing either 11D5-3-CD8BBZ, FHVH33-CD8BBZ, or FHVH33-CD828Z CAR had eradication of tumors.

The survival of the mice is shown in FIG. 10B. Mice receiving T cells expressing either 11D5-3-CD8BBZ, FHVH33-CD8BBZ, or FHVH33-CD828Z CAR survived.

Example 11

This example demonstrates that T cells expressing heavy-chain-only CARs release IFN-gamma in a BCMA-specific manner.

Effector T cells were cultured overnight with the target cells indicated in Table 5. Effector T cells were either untransduced T cells, T cells transduced with a nucleotide sequence encoding FHVH33-CD828Z, or T cells transduced with a nucleotide sequence encoding FHVH33-CD8BBZ. T cells were all from the same human donor. FHVH33-CD828Z-transduced T cells provided 71% CAR expression. FHVH33-CD8BBZ-transduced T cells provided 80% CAR expression.

The BCMA+ target cells were BCMA-K562 and RPMI8226. The BCMA-negative target cells were Panc10.05, U251, 293GP, primary normal human bronchial epithelial cells (NHBE), primary human microvascular endothelial cells (HMVEC), primary human intestinal epithelial cells (InEpC).

An interferon (IFN)-gamma ELISA was performed. The results are shown in Table 5. Interferon gamma production by effector T cells alone is also shown in Table 5. All values in Table 5 are pg/mL of IFN-gamma.

TABLE 5

| | | Effector T cell | | |
|---|---|---|---|---|
| | | Untransduced | FHVH33-828Z | FHVH33-8BBZ |
| BCMA+ | BCMA-K562 | 179 | 38548 | 70216 |
| | RPMI-8226 | 406 | 13855 | 33465 |
| BCMA- | Panc10.05 | 76 | 37 | 306 |
| negative | U251 | 41 | 24 | 360 |
| | 293GP | 92 | 40 | 238 |
| | NHBE | 54 | 43 | 423 |
| | HMVEC | 54 | 25 | 610 |
| | InEpC | 33 | 18 | 500 |
| Control | T-cells only | 25 | 14 | 367 |

As shown in Table 5, the CAR T cells produced much more interferon gamma in the presence of BCMA+ targets.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

SEQUENCE LISTING

Sequence total quantity: 42
SEQ ID NO: 1                    moltype = AA   length = 8
FEATURE                         Location/Qualifiers
source                          1..8
                                mol_type = protein
                                organism = Homo sapiens
SEQUENCE: 1
GFTFTNHA                                                                   8

SEQ ID NO: 2                    moltype = AA   length = 8
FEATURE                         Location/Qualifiers
source                          1..8
                                mol_type = protein
                                organism = Homo sapiens
SEQUENCE: 2
ISGNGRTT                                                                   8

SEQ ID NO: 3                    moltype = AA   length = 11
FEATURE                         Location/Qualifiers
source                          1..11
                                mol_type = protein
                                organism = Homo sapiens
SEQUENCE: 3
AKDGGETLVD S                                                               11

SEQ ID NO: 4                    moltype = AA   length = 8
FEATURE                         Location/Qualifiers
source                          1..8
                                mol_type = protein
                                organism = Homo sapiens
SEQUENCE: 4
GFTFSSHA                                                                   8

SEQ ID NO: 5                    moltype = AA   length = 8
FEATURE                         Location/Qualifiers
source                          1..8
                                mol_type = protein
                                organism = Homo sapiens
SEQUENCE: 5
ISGSGDFT                                                                   8

SEQ ID NO: 6                    moltype = AA   length = 12
FEATURE                         Location/Qualifiers
source                          1..12
                                mol_type = protein
                                organism = Homo sapiens
SEQUENCE: 6
AKDEDGGSLL GY                                                              12

SEQ ID NO: 7                    moltype = AA   length = 8
FEATURE                         Location/Qualifiers
source                          1..8
                                mol_type = protein
                                organism = Homo sapiens
SEQUENCE: 7
GFTFSSYA                                                                   8

SEQ ID NO: 8                    moltype = AA   length = 8
FEATURE                         Location/Qualifiers
source                          1..8
                                mol_type = protein
                                organism = Homo sapiens
SEQUENCE: 8
ISGSGDYI                                                                   8

SEQ ID NO: 9                    moltype = AA   length = 14
FEATURE                         Location/Qualifiers
source                          1..14
                                mol_type = protein
                                organism = Homo sapiens
SEQUENCE: 9
AKEGTGANSS LADY                                                            14

SEQ ID NO: 10                   moltype = AA   length = 8
FEATURE                         Location/Qualifiers
source                          1..8
                                mol_type = protein
                                organism = Homo sapiens -continued

```
SEQUENCE: 10
GFTFSSHA                                                                        8

SEQ ID NO: 11          moltype = AA  length = 8
FEATURE                Location/Qualifiers
source                 1..8
                       mol_type = protein
                       organism = Homo sapiens
SEQUENCE: 11
ISGSGDYT                                                                        8

SEQ ID NO: 12          moltype = AA  length = 12
FEATURE                Location/Qualifiers
source                 1..12
                       mol_type = protein
                       organism = Homo sapiens
SEQUENCE: 12
AKDEDGGSLL GH                                                                   12

SEQ ID NO: 13          moltype = AA  length = 118
FEATURE                Location/Qualifiers
source                 1..118
                       mol_type = protein
                       organism = Homo sapiens
SEQUENCE: 13
QVQLVESGGG LVQPGGSLRL SCAASGFTFT NHAMSWVRQA PGKGLELVSS ISGNGRTTYY              60
ADSVKGRFTI SRDISKNTLD LQMNSLRAED TAVYYCAKDG GETLVDSRGQ GTLVTVSS               118

SEQ ID NO: 14          moltype = AA  length = 119
FEATURE                Location/Qualifiers
source                 1..119
                       mol_type = protein
                       organism = Homo sapiens
SEQUENCE: 14
QVQLVESGGG LVQPGGSLRL SCAASGFTFS SHAMTWVRQA PGKGLEWVAA ISGSGDFTHY              60
ADSVKGRFTI SRDNSKNTVS LQMNNLRAED TAVYYCAKDE DGGSLLGYRG QGTLVTVSS              119

SEQ ID NO: 15          moltype = AA  length = 121
FEATURE                Location/Qualifiers
source                 1..121
                       mol_type = protein
                       organism = Homo sapiens
SEQUENCE: 15
EVQLLESGGG LVQPGGSLRL SCAASGFTFS SYAMSWVRQA PGKGLEWVSS ISGSGDYIYY              60
ADSVKGRFTI SRDISKNTLY LQMNSLRAED TAVYYCAKEG TGANSSLADY RGQGTLVTVS             120
S                                                                              121

SEQ ID NO: 16          moltype = AA  length = 119
FEATURE                Location/Qualifiers
source                 1..119
                       mol_type = protein
                       organism = Homo sapiens
SEQUENCE: 16
EVQLLESGGG LIQPGGSLRL SCAASGFTFS SHAMTWVRQA PGKGLEWVSA ISGSGDYTHY              60
ADSVKGRFTI SRDNSKNTVY LQMNSLRAED SAVYYCAKDE DGGSLLGHRG QGTLVTVSS              119

SEQ ID NO: 17          moltype = AA  length = 375
FEATURE                Location/Qualifiers
REGION                 1..375
                       note = Synthetic
source                 1..375
                       mol_type = protein
                       organism = synthetic construct
SEQUENCE: 17
MALPVTALLL PLALLLHAAR PQVQLVESGG GLVQPGGSLR LSCAASGFTF TNHAMSWVRQ              60
APGKGLELVS SISGNGRTTY YADSVKGRFT ISRDISKNTL DLQMNSLRAE DTAVYYCAKD             120
GGETLVDSRG QGTLVTVSSF VPVFLPAKPT TTPAPRPPTP APTIASQPLS LRPEACRPAA             180
GGAVHTRGLD FACDIYIWAP LAGTCGVLLL SLVITLYCNH RNRSKRSRLL HSDYMNMTPR             240
RPGPTRKHYQ PYAPPRDFAA YRSRVKFSRS ADAPAYQQGQ NQLYNELNLG RREEYDVLDK             300
RRGRDPEMGG KPRRKNPQEG LYNELQKDKM AEAYSEIGMK GERRRGKGHD GLYQGLSTAT             360
KDTYDALHMQ ALPPR                                                              375

SEQ ID NO: 18          moltype = AA  length = 376
FEATURE                Location/Qualifiers
REGION                 1..376
                       note = Synthetic
source                 1..376
                       mol_type = protein
                       organism = synthetic construct
```

-continued

```
SEQUENCE: 18
MALPVTALLL PLALLLHAAR PQVQLVESGG GLVQPGGSLR LSCAASGFTF SSHAMTWVRQ    60
APGKGLEWVA AISGSGDFTH YADSVKGRFT ISRDNSKNTV SLQMNNLRAE DTAVYYCAKD   120
EDGGSLLGYR GQGTLVTVSS FVPVFLPAKP TTTPAPRPPT PAPTIASQPL SLRPEACRPA   180
AGGAVHTRGL DFACDIYIWA PLAGTCGVLL LSLVITLYCN HRNRSKRSRL LHSDYMNMTP   240
RRPGPGTRKHY QPYAPPRDFA AYRSRVKFSR SADAPAYQQG QNQLYNELNL GRREEYDVLD   300
KRRGRDPEMG GKPRRKNPQE GLYNELQKDK MAEAYSEIGM KGERRRGKGH DGLYQGLSTA   360
TKDTYDALHM QALPPR                                                   376

SEQ ID NO: 19          moltype = AA  length = 378
FEATURE                Location/Qualifiers
REGION                 1..378
                       note = Synthetic
source                 1..378
                       mol_type = protein
                       organism = synthetic construct
SEQUENCE: 19
MALPVTALLL PLALLLHAAR PEVQLLESGG GLVQPGGSLR LSCAASGFTF SSYAMSWVRQ    60
APGKGLEWVS SISGSGDYIY YADSVKGRFT ISRDISKNTL YLQMNSLRAE DTAVYYCAKE   120
GTGANSSLAD YRGQGTLVTV SSFVPVFLPA KPTTTPAPRP PTPAPTIASQ PLSLRPEACR   180
PAAGGAVHTR GLDFACDIYI WAPLAGTCGV LLLSLVITLY CNHRNRSKRS RLLHSDYMNM   240
TPRRPGPTRK HYQPYAPPRD FAAYRSRVKF SRSADAPAYQ QGQNQLYNEL NLGRREEYDV   300
LDKRRGRDPE MGGKPRRKNP QEGLYNELQK DKMAEAYSEI GMKGERRRGK GHDGLYQGLS   360
TATKDTYDAL HMQALPPR                                                 378

SEQ ID NO: 20          moltype = AA  length = 376
FEATURE                Location/Qualifiers
REGION                 1..376
                       note = Synthetic
source                 1..376
                       mol_type = protein
                       organism = synthetic construct
SEQUENCE: 20
MALPVTALLL PLALLLHAAR PEVQLLESGG GLIQPGGSLR LSCAASGFTF SSHAMTWVRQ    60
APGKGLEWVS AISGSGDYTH YADSVKGRFT ISRDNSKNTV YLQMNSLRAE DSAVYYCAKD   120
EDGGSLLGHR GQGTLVTVSS FVPVFLPAKP TTTPAPRPPT PAPTIASQPL SLRPEACRPA   180
AGGAVHTRGL DFACDIYIWA PLAGTCGVLL LSLVITLYCN HRNRSKRSRL LHSDYMNMTP   240
RRPGPTRKHY QPYAPPRDFA AYRSRVKFSR SADAPAYQQG QNQLYNELNL GRREEYDVLD   300
KRRGRDPEMG GKPRRKNPQE GLYNELQKDK MAEAYSEIGM KGERRRGKGH DGLYQGLSTA   360
TKDTYDALHM QALPPR                                                   376

SEQ ID NO: 21          moltype = AA  length = 376
FEATURE                Location/Qualifiers
REGION                 1..376
                       note = Synthetic
source                 1..376
                       mol_type = protein
                       organism = synthetic construct
SEQUENCE: 21
MALPVTALLL PLALLLHAAR PQVQLVESGG GLVQPGGSLR LSCAASGFTF TNHAMSWVRQ    60
APGKGLELVS SISGNGRTTY YADSVKGRFT ISRDISKNTL DLQMNSLRAE DTAVYYCAKD   120
GGETLVDSRG QGTLVTVSSF VPVFLPAKPT TTPAPRPPTP APTIASQPLS LRPEACRPAA   180
GGAVHTRGLD FACDIYIWAP LAGTCGVLLL SLVITLYCNH RNKRGRKKLL YIFKQPFMRP   240
VQTTQEEDGC SCRFPEEEEG GCELRVKFSR SADAPAYQQG QNQLYNELNL GRREEYDVLD   300
KRRGRDPEMG GKPRRKNPQE GLYNELQKDK MAEAYSEIGM KGERRRGKGH DGLYQGLSTA   360
TKDTYDALHM QALPPR                                                   376

SEQ ID NO: 22          moltype = AA  length = 377
FEATURE                Location/Qualifiers
REGION                 1..377
                       note = Synthetic
source                 1..377
                       mol_type = protein
                       organism = synthetic construct
SEQUENCE: 22
MALPVTALLL PLALLLHAAR PQVQLVESGG GLVQPGGSLR LSCAASGFTF SSHAMTWVRQ    60
APGKGLEWVA AISGSGDFTH YADSVKGRFT ISRDNSKNTV SLQMNNLRAE DTAVYYCAKD   120
EDGGSLLGYR GQGTLVTVSS FVPVFLPAKP TTTPAPRPPT PAPTIASQPL SLRPEACRPA   180
AGGAVHTRGL DFACDIYIWA PLAGTCGVLL LSLVITLYCN HRNKRGRKKL LYIFKQPFMR   240
PVQTTQEEDG CSCRFPEEEE GGCELRVKFS RSADAPAYQQ GQNQLYNELN LGRREEYDVL   300
DKRRGRDPEM GGKPRRKNPQ EGLYNELQKD KMAEAYSEIG MKGERRRGKG HDGLYQGLST   360
ATKDTYDALH MQALPPR                                                  377

SEQ ID NO: 23          moltype = AA  length = 379
FEATURE                Location/Qualifiers
REGION                 1..379
                       note = Synthetic
source                 1..379
                       mol_type = protein
```

```
                           organism = synthetic construct
SEQUENCE: 23
MALPVTALLL PLALLLHAAR PEVQLLESGG GLVQPGGSLR LSCAASGFTF SSYAMSWVRQ    60
APGKGLEWVS SISGSGDYIY YADSVKGRFT ISRDISKNTL YLQMNSLRAE DTAVYYCAKE   120
GTGANSSLAD YRGQGTLVTV SSFVPVFLPA KPTTTPAPRP PTPAPTIASQ PLSLRPEACR   180
PAAGGAVHTR GLDFACDIYI WAPLAGTCGV LLLSLVITLY CNHRNKRGRK KLLYIFKQPF   240
MRPVQTTQEE DGCSCRFPEE EEGGCELRVK FSRSADAPAY QQGQNQLYNE LNLGRREEYD   300
VLDKRRGRDP EMGGKPRRKN PQEGLYNELQ KDKMAEAYSE IGMKGERRRG KGHDGLYQGL   360
STATKDTYDA LHMQALPPR                                               379

SEQ ID NO: 24              moltype = AA   length = 377
FEATURE                    Location/Qualifiers
REGION                     1..377
                           note = Synthetic
source                     1..377
                           mol_type = protein
                           organism = synthetic construct
SEQUENCE: 24
MALPVTALLL PLALLLHAAR PEVQLLESGG GLIQPGGSLR LSCAASGFTF SSHAMTWVRQ    60
APGKGLEWVS AISGSGDYTH YADSVKGRFT ISRDNSKNTV YLQMNSLRAE DSAVYYCAKD   120
EDGGSLLGHR GQGTLVTVSS FVPVFLPAKP TTTPAPRPPT PAPTIASQPL SLRPEACRPA   180
AGGAVHTRGL DFACDIYIWA PLAGTCGVLL LSLVITLYCN HRNKRGRKKL YIFKQPFMR    240
PVQTTQEEDG CSCRFPEEEE GGCELRVKFS RSADAPAYQQ GQNQLYNELN LGRREEYDVL   300
DKRRGRDPEM GGKPRRKNPQ EGLYNELQKD KMAEAYSEIG MKGERRRGKG HDGLYQGLST   360
ATKDTYDALH MQALPPR                                                 377

SEQ ID NO: 25              moltype = AA   length = 372
FEATURE                    Location/Qualifiers
REGION                     1..372
                           note = Synthetic
source                     1..372
                           mol_type = protein
                           organism = synthetic construct
SEQUENCE: 25
MALPVTALLL PLALLLHAAR PQVQLVESGG GLVQPGGSLR LSCAASGFTF TNHAMSWVRQ    60
APGKGLELVS SISGNGRTTY YADSVKGRFT ISRDISKNTL DLQMNSLRAE DTAVYYCAKD   120
GGETLVDSRG QGTLVTVSSF VPVFLPAKPT TTPAPRPPTP APTIASQPLS LRPEACRPAA   180
GGAVHTRGLD FACDIYIWAP LAGTCGVLLL SLVITLYCNH RNCWLTKKKY SSSVHDPNGE   240
YMFMRAVNTA KKSRLTDVTL RVKFSRSADA PAYQQGQNQL YNELNLGRRE EYDVLDKRRG   300
RDPEMGGKPR RKNPQEGLYN ELQKDKMAEA YSEIGMKGER RRGKGHDGLY QGLSTATKDT   360
YDALHMQALP PR                                                      372

SEQ ID NO: 26              moltype = AA   length = 373
FEATURE                    Location/Qualifiers
REGION                     1..373
                           note = Synthetic
source                     1..373
                           mol_type = protein
                           organism = synthetic construct
SEQUENCE: 26
MALPVTALLL PLALLLHAAR PQVQLVESGG GLVQPGGSLR LSCAASGFTF SSHAMTWVRQ    60
APGKGLEWVA AISGSGDFTH YADSVKGRFT ISRDNSKNTV SLQMNNLRAE DTAVYYCAKD   120
EDGGSLLGYR GQGTLVTVSS FVPVFLPAKP TTTPAPRPPT PAPTIASQPL SLRPEACRPA   180
AGGAVHTRGL DFACDIYIWA PLAGTCGVLL LSLVITLYCN HRNCWLTKKK YSSSVHDPNG   240
EYMFMRAVNT AKKSRLTDVT LRVKFSRSAD APAYQQGQNQ LYNELNLGRR EEYDVLDKRR   300
GRDPEMGGKP RRKNPQEGLY NELQKDKMAE AYSEIGMKGE RRRGKGHDGL YQGLSTATKD   360
TYDALHMQAL PPR                                                     373

SEQ ID NO: 27              moltype = AA   length = 375
FEATURE                    Location/Qualifiers
REGION                     1..375
                           note = Synthetic
source                     1..375
                           mol_type = protein
                           organism = synthetic construct
SEQUENCE: 27
MALPVTALLL PLALLLHAAR PEVQLLESGG GLVQPGGSLR LSCAASGFTF SSYAMSWVRQ    60
APGKGLEWVS SISGSGDYIY YADSVKGRFT ISRDISKNTL YLQMNSLRAE DTAVYYCAKE   120
GTGANSSLAD YRGQGTLVTV SSFVPVFLPA KPTTTPAPRP PTPAPTIASQ PLSLRPEACR   180
PAAGGAVHTR GLDFACDIYI WAPLAGTCGV LLLSLVITLY CNHRNCWLTK KKYSSSVHDP   240
NGEYMFMRAV NTAKKSRLTD VTLRVKFSRS ADAPAYQQGQ NQLYNELNLG RREEYDVLDK   300
RRGRDPEMGG KPRRKNPQEG LYNELQKDKM AEAYSEIGMK GERRRGKGHD GLYQGLSTAT   360
KDTYDALHMQ ALPPR                                                   375

SEQ ID NO: 28              moltype = AA   length = 373
FEATURE                    Location/Qualifiers
REGION                     1..373
                           note = Synthetic
source                     1..373
```

```
                              mol_type = protein
                              organism = synthetic construct
        SEQUENCE: 28
        MALPVTALLL PLALLLHAAR PEVQLLESGG GLIQPGGSLR LSCAASGFTF SSHAMTWVRQ    60
        APGKGLEWVS AISGSGDYTH YADSVKGRFT ISRDNSKNTV YLQMNSLRAE DSAVYYCAKD   120
        EDGGSLLGHR GQGTLVTVSS FVPVFLPAKP TTTPAPRPPT PAPTIASQPL SLRPEACRPA   180
        AGGAVHTRGL DFACDIYIWA PLAGTCGVLL LSLVITLYCN HRNCWLTKKK YSSSVHDPNG   240
        EYMFMRAVNT AKKSRLTDVT LRVKFSRSAD APAYQQGQNQ LYNELNLGRR EEYDVLDKRR   300
        GRDPEMGGKP RRKNPQEGLY NELQKDKMAE AYSEIGMKGE RRRGKGHDGL YQGLSTATKD   360
        TYDALHMQAL PPR                                                     373

SEQ ID NO: 29         moltype = DNA   length = 1128
        FEATURE               Location/Qualifiers
        misc_feature          1..1128
                              note = Synthetic
        source                1..1128
                              mol_type = other DNA
                              organism = synthetic construct
        SEQUENCE: 29
        atggccctgc ctgttacagc tctgctgctg cctctggctc tgcttctgca tgccgccaga    60
        cctcaggtgc agctggtgga gtctggggga ggcttggtac agcctggggg gtccctgaga   120
        ctctcctgtg cagcctctgg attcaccttt accaaccatg ccatgagttg ggtccgccag   180
        gctccaggga aggggctgga gttggtgtct cagtattagt gtaatggtcg taccacatac   240
        tacgcagact ccgtgaaggg ccggttcacc atctccagag acattccaa gaacacgctg    300
        gatctgcaaa tgaacagcct gagagccgag gacacggccg tatattactg tgcgaaagat   360
        gggggcgaaa ctctagttga ctccagaggc cagggcaccc tggtcaccgt ctcctcattc   420
        gtgcccgtgt tcctgcctgc caagcctaca acaaccctg ctcctagacc tcctacacca    480
        gctcctacaa tcgccagcca gcctctgtct ctgaggcctg aagcttgtag acctgctgct   540
        ggcggagccg tgcataccag aggactggat ttcgcctgcg acatctacat ctgggcccct   600
        ctggctggaa catgtggcgt tttgctgctg agcctcgtga tcaccctg gtactgcaac     660
        cggaacagaa gcaagcggag ccggctgctg cacagcgact acatgaacat gaccccaga    720
        cggcctggcc ccaccagaaa gcactaccag ccttacgccc tcccagaga cttcgccgcc    780
        taccggtcca gagtgaagtt cagcagaagc gccgacgccc tgccatatca gcagggccag   840
        aaccagctgt acaacgagct gaacctgggc agacgggaga agtacgatgt gctggacaaa   900
        agacgtggcc gggaccctga gatgggggga aagccgagaa ggaagaaccc tcaggaaggc   960
        ctgtacaatg aactgcagaa agataagatg gcggaggcct acagtgagat tgggatgaaa  1020
        ggcgagcgcc ggagggggca aggggcacgat ggcctttacc agggtctcag tacagccacc  1080
        aaggacacct acgacgccct tcacatgcag gccctgcccc ctcgctaa             1128

SEQ ID NO: 30         moltype = DNA   length = 1131
        FEATURE               Location/Qualifiers
        misc_feature          1..1131
                              note = Synthetic
        source                1..1131
                              mol_type = other DNA
                              organism = synthetic construct
        SEQUENCE: 30
        atggccctgc ctgttacagc tctgctgctg cctctggctc tgcttctgca tgccgccaga    60
        cctcaggtgc agctggtgga gtctggggga ggcttggtac agcctggggg gtccctgaga   120
        ctctcctgtg cagcctctgg attcaccttt agcagccatg ccatgacctg ggtccgccag   180
        gctccgggga aggggctgga gtgggtcgca gctattagtg gcagtggtga tttcacacac   240
        tacgcagact ccgtgaaggg ccggttcacc atctccagag acaattccaa gaacacggtg   300
        tctctgcaaa tgaacaacct gagagccgag gacacggccg tatattactg tgcgaaagat   360
        gaggatggtg gagcttgct tggctacaga ggccagggca ccctggtcac cgtctcctca    420
        ttcgtgcccg tgttcctgcc tgccaagcct acaacaaccc tgctcctag acctcctaca    480
        ccagctccta caatcgccag ccagcctctg tctctgaggc tgaagcttg tagacctgct    540
        gctggcggag ccgtgcatac cagaggactg gatttcgcct gcgacatcta catctgggcc   600
        cctctggctg gaacatgtgg cgttttgctg ctgagcctcg tgatcaccct gtactgcaac   660
        caccggaaca gaagcaagcg gagccggctg cacagcgact acatgaacat gaccccagaa   720
        cggcctggcc gccccaccag aaagcactac cagccttacg ccctcccag agacttcgcc    780
        gcctaccggt ccagagtgaa gttcagcaga agcgccgacg ccctgcccta tcagcagggc   840
        cagaaccagc tgtacaacga gctgaacctg gcagacgggg aagagtacga gtgctggac    900
        aaaagacgtg gccgggaccc tgagatgggg ggaaagccga gaaggaagaa ccctcaggaa   960
        ggcctgtaca atgaactgca gaaagataag atggcggagg cctacagtga gattgggatg  1020
        aaaggcgagc gccggagggg caaggggcac gatggccttt accagggtct cagtacagcc  1080
        accaaggaca cctacgacgc ccttcacatg caggccctgc cccctcgcta a           1131

SEQ ID NO: 31         moltype = DNA   length = 1137
        FEATURE               Location/Qualifiers
        misc_feature          1..1137
                              note = Synthetic
        source                1..1137
                              mol_type = other DNA
                              organism = synthetic construct
        SEQUENCE: 31
        atggccctgc ctgttacagc tctgctgctg cctctggctc tgcttctgca tgccgccaga    60
        cctgaggtgc agctgttgga gtctggggga ggcttggtac agcctggggg gtccctgaga   120
        ctctcctgtg cagcctctgg attcaccttt agcagctatg ccatgagctg ggtccgccag   180
        gctccaggga aggggctgga gtgggtctca tctattagtg gtagtggtga ttacatatac   240
```

-continued

```
tacgcagact ccgtgaaggg ccggttcacc atctccagag acatatccaa gaacacgctg    300
tatctgcaaa tgaacagcct gagagccgag gacacggccg tatattactg tgcgaaagaa    360
ggtacgggtg ccaacagcag cttggcagac tacagaggcc agggcaccct ggtcaccgtc    420
tcctcattcg tgcccgtgtt cctgcctgcc aagcctacaa caacccctgc tcctagacct    480
cctacaccag ctcctacaat cgccacccag cctctgtctc tgaggcctga agcttgtaga    540
cctgctgctg gcggagccgt gcataccaga ggactggatt cgcctgcga catctcatc    600
tgggcccctc tggctggaac atgtggcgtt ttgctgctga gcctcgtgat caccctgtac    660
tgcaaccacc ggaacagaag caagcggagc cggctgctgc acagcgacta catgaacatg    720
accccagac ggcctggccc caccagaaag cactaccagc cttacgcccc tcccagagac    780
ttcgccgcct accggtccag agtgaagttc agcagaagcg ccgacgcccc tgcctatcag    840
cagggccaga accagctgta caacgagctg aacctgggca gacgggaaga gtacgatgtg    900
ctggacaaaa gacgtggccg ggaccctgag atggggggaa agccgagaag gaagaaccct    960
caggaaggcc tgtacaatga actgcagaaa gataagatgg cggaggccta cagtgagatt    1020
gggatgaaag gcgagcgccg gaggggcaag gggcacgatg gcctttacca gggtctcagt    1080
acagccacca aggacaccta cgacgccctt cacatgcagg ccctgccccc tcgctaa    1137
```

```
SEQ ID NO: 32               moltype = DNA   length = 1131
FEATURE                     Location/Qualifiers
misc_feature                1..1131
                            note = Synthetic
source                      1..1131
                            mol_type = other DNA
                            organism = synthetic construct
SEQUENCE: 32
atggccctgc ctgttacagc tctgctgctg cctctggctc tgcttctgca tgccgccaga    60
cctgaggtgc agctgttgga gtctggggga ggcttgatac agcctggggg gtccctgaga    120
ctctcctgtg cagcctctgg attcaccttt agcagccatg ccatgacctg ggtccgccag    180
gctccgggga aggggctgga gtgggtctca gctattagtg gtagtggtga ttacacacac    240
tacgcagact ccgtgaaggg tcggttcacc atctccagag acaattccaa gaacacggtg    300
tatctccaaa tgaacagtct gagagccgag gactcggccg tatattactg tgcgaaagat    360
gaggatggtg ggagcctcct ggggcacaga ggccagggca ccctggtcac cgtctcctca    420
ttcgtgcccg tgttcctgcc tgccaagcct acaacaaccc ctgctcctag acctcctaca    480
ccagctccta caatcgccag ccagcctctg tctctgaggc ctgaagcttg tagacctgct    540
gctggcggag ccgtgcatac cagaggactg gatttcgcct gcgacatcta catctgggct    600
cctctggctg gaacatgtgg cgttttgctg ctgagcctcg tgatcaccct gtactgcaac    660
caccggaaca gaagcaagcg gagccggctg ctgcacagcg actacatgaa catgaccccc    720
agacggcctg gccccaccag aaagcactac cagccttacg cccctcccag agacttcgcc    780
gcctaccggt ccagagtgaa gttcagcaga agcgccgacg cccctgccta tcagcagggc    840
cagaaccagc tgtacaacga gctgaacctg ggcagacggg aagagtacga tgtgctggac    900
aaaagacgtg gccgggaccc tgagatgggg ggaaagccga aggaagaa ccctcaggaa    960
ggcctgtaca tgaactgca gaaagataag atggcggagg cctacagtga gattgggatg    1020
aaaggcgagc gccggagggg caaggggcac gatggccttt accagggtct cagtacagcc    1080
accaaggaca cctacgacgc ccttcacatg caggccctgc ccctcgcta a    1131
```

```
SEQ ID NO: 33               moltype = DNA   length = 1131
FEATURE                     Location/Qualifiers
misc_feature                1..1131
                            note = Synthetic
source                      1..1131
                            mol_type = other DNA
                            organism = synthetic construct
SEQUENCE: 33
atggccctgc ctgttacagc tctgctgctg cctctggctc tgcttctgca tgccgccaga    60
cctcaggtgc agctggtgga gtctggggga ggcttggtac agcctggggg gtccctgaga    120
ctctcctgtg cagcctctgg attcaccttt accaaccatg ccatgagttg ggtccgccag    180
gctccaggga aggggctgga gttggtctca agtattagtg gtaatggtcg taccacatac    240
tacgcagact ccgtgaaggg ccggttcacc atctccagag acatttccaa gaacacgctg    300
gatctgcaaa tgaacagcct gagagccgag gacacggccg tatattactg tgcgaaagat    360
gggggcgaaa ctctagttga ctccagaggc cagggcaccc tggtcaccgt ctcctcattc    420
gtgcccgtgt tcctgcctgc caagcctaca acaaccccctg ctcctagacc tcctacacca    480
gctcctacaa tcgccagcca gcctctgtct ctgaggcctg aagcttgtag acctgctgct    540
ggcggagccg tgcataccag aggactggat ttcgcctgcg acatctacat ctgggcccct    600
ctggctggaa catgtggcgt tttgctgctg agcctcgtga tcaccctgta ctgcaaccac    660
cggaacaagc ggggccagaaa gaagctgctg tacatcttca gcagcccctt catgcggccc    720
gtgcagacca cccaggaaga ggacggctgc tcctgcagat tccccgagga agaagaaggc    780
ggctgcgagc tgagagtgaa gttcagcaga agcgccgacg cccctgccta tcagcagggc    840
cagaaccagc tgtacaacga gctgaacctg ggcagacggg aagagtacga tgtgctggac    900
aaaagacgtg gccgggaccc tgagatgggg ggaaagccga aggaagaa ccctcaggaa    960
ggcctgtaca tgaactgca gaaagataag atggcggagg cctacagtga gattgggatg    1020
aaaggcgagc gccggagggg caaggggcac gatggccttt accagggtct cagtacagcc    1080
accaaggaca cctacgacgc ccttcacatg caggccctgc ccctcgcta a    1131
```

```
SEQ ID NO: 34               moltype = DNA   length = 1134
FEATURE                     Location/Qualifiers
misc_feature                1..1134
                            note = Synthetic
source                      1..1134
                            mol_type = other DNA
                            organism = synthetic construct
```

```
SEQUENCE: 34
atggccctgc ctgttacagc tctgctgctg cctctggctc tgcttctgca tgccgccaga   60
cctcaggtgc agctggtgga gtctggggga ggcttggtac agcctggggg gtccctgaga  120
ctctcctgtg cagcctctgg attcaccttt agcagccatg ccatgacctg ggtccgccag  180
gctccgggga aggggctgga gtgggtcgca gctattagtg gcagtggtga tttcacacac  240
tacgcagact ccgtgaaggg ccggttcacc atctccagag acaattccaa gaacacggtg  300
tctctgcaaa tgaacaacct gagagccgag gacacggccg tatattactg tgcgaaagat  360
gaggatggtg ggagcttgct tggctacaga ggccagggca ccctggtcac cgtctcctca  420
ttcgtgcccg tgttcctgcc tgccaagcct acaacaaccc ctgctcctag acctcctaca  480
ccagctccta caatcgccag ccagcctctg tctctgaggc ctgaagcttg tagacctgct  540
gctggcggag ccgtgcatac cagaggactg atttcgcct gcgacatcta catctgggcc  600
cctctggctg aacatgtgg cgttttgctg ctgagcctcg tgatcaccct gtactgcaac  660
caccggaaca agcggggcag aaagaagctg ctgtacatct tcaagcagcc cttcatgcgg  720
cccgtgcaga ccacccagga agaggacggc tgctcctgca gattccccga ggaagaagaa  780
ggcggctgcg agctgagagt gaagttcagc agaagcgccg acgcccctgc ctatcagcag  840
ggccagaacc agctgtacaa cgagctgaac ctgggcagac gggaagagta cgatgtgctg  900
gacaaaagac gtggccggga ccctgagatg gggggaaagc cgagaaggaa gaaccctcag  960
gaaggcctgt acaatgaact gcagaaagat aagatggcgg aggctacag tgagattggg 1020
atgaaaggcg agcgccggag gggcaagggg cacgatggcc tttaccaggg tctcagtaca 1080
gccaccaagg acacctacga cgcccttcac atgcaggccc tgcccctcg ctaa         1134

SEQ ID NO: 35        moltype = DNA  length = 1140
FEATURE              Location/Qualifiers
misc_feature        1..1140
                     note = Synthetic
source               1..1140
                     mol_type = other DNA
                     organism = synthetic construct
SEQUENCE: 35
atggccctgc ctgttacagc tctgctgctg cctctggctc tgcttctgca tgccgccaga   60
cctgaggtgc agctgttgga gtctggggga ggcttggtac agcctggggg gtccctgaga  120
ctctcctgtg cagcctctgg attcaccttt agcagctatg ccatgagctg ggtccgccag  180
gctccaggga aggggctgga gtgggtctca tctattagtg gtagtggtga ttacatatac  240
tacgcagact ccgtgaaggg ccggttcacc atctccagag acaatatccaa gaacacgctg  300
tatctgcaaa tgaacagcct gagagccgag gacacggccg tatattactg tgcgaaagaa  360
ggtacgggtg ccaacagcag cttggcgac tacagaggcc agggcaccct ggtcaccgtc  420
tcctcattcg tgcccgtgtt cctgcctgcc aagcctacaa caaccctgc tcctagacct  480
cctacaccag ctcctacaat cgccagccag cctctgtctc tgaggcctga agcttgtaga  540
cctgctgctg gcggagccgt gcataccaga ggactggatt tcgcctgcga catctacatc  600
tgggcccctc tggctggaac atgtggcgtt ttgctgctga gcctcgtgat caccctgtac  660
tgcaaccacc ggaacaagcg gggcagaaag aagctgctgt acatcttcaa gcagcccttc  720
atgcggcccg tgcagaccac ccaggaagag gacggctgct cctgcagatt ccccgaggaa  780
gaagaaggcg gctgcgagct gagagtgaag ttcagcagaa gcgccgacgc ccctgcctat  840
cagcagggcc agaaccagct gtacaacgag ctgaacctgg gcagacggga agagtacgat  900
gtgctggaca aaagacgtgg ccgggaccct gagatggggg gaaagccgag aaggaagaac  960
cctcaggaag gcctgtacaa tgaactgcag aaagataaga tggcggaggc ctacagtgag 1020
attgggatga aggcgagcg ccggaggggc aaggggcacg atggccttta ccagggtctc 1080
agtacagcca ccaaggacac ctacgacgcc cttcacatgc aggccctgcc cctcgctaa  1140

SEQ ID NO: 36        moltype = DNA  length = 1134
FEATURE              Location/Qualifiers
misc_feature        1..1134
                     note = Synthetic
source               1..1134
                     mol_type = other DNA
                     organism = synthetic construct
SEQUENCE: 36
atggccctgc ctgttacagc tctgctgctg cctctggctc tgcttctgca tgccgccaga   60
cctgaggtgc agctgttgga gtctggggg ggcttgatac agcctggggg gtccctgaga  120
ctctcctgtg cagcctctgg attcaccttt agcagccatg ccatgacctg ggtccgccag  180
gctccgggga aggggctgga gtgggtctca gctattagtg gtagtggtga ttacacacac  240
tacgcagact ccgtgaaggg tcggttcacc atctccagag acaattccaa gaacacggtg  300
tatctccaaa tgaacagtct gagagccgag gactcggccg tatattactg tgcgaaagat  360
gaggatggtg ggagcctcct ggggcacaga ggccagggca ccctggtcac cgtctcctca  420
ttcgtgcccg tgttcctgcc tgccaagcct acaacaaccc ctgctcctag acctcctaca  480
ccagctccta caatcgccag ccagcctctg tctctgaggc ctgaagcttg tagacctgct  540
gctggcggag ccgtgcatac cagaggactg atttcgcct gcgacatcta catctgggcc  600
cctctggctg aacatgtgg cgttttgctg ctgagcctcg tgatcaccct gtactgcaac  660
caccggaaca agcggggcag aaagaagctg ctgtacatct tcaagcagcc cttcatgcgg  720
cccgtgcaga ccacccagga agaggacggc tgctcctgca gattccccga ggaagaagaa  780
ggcggctgcg agctgagagt gaagttcagc agaagcgccg acgcccctgc ctatcagcag  840
ggccagaacc agctgtacaa cgagctgaac ctgggcagac gggaagagta cgatgtgctg  900
gacaaaagac gtggccggga ccctgagatg gggggaaagc cgagaaggaa gaaccctcag  960
gaaggcctgt acaatgaact gcagaaagat aagatggcgg aggctacag tgagattggg 1020
atgaaaggcg agcgccggag gggcaagggg cacgatggcc tttaccaggg tctcagtaca 1080
gccaccaagg acacctacga cgcccttcac atgcaggccc tgcccctcg ctaa         1134

SEQ ID NO: 37        moltype = DNA  length = 1119
FEATURE              Location/Qualifiers
```

-continued

```
misc_feature          1..1119
                      note = Synthetic
source                1..1119
                      mol_type = other DNA
                      organism = synthetic construct
SEQUENCE: 37
atggccctgc ctgttacagc tctgctgctg cctctggctc tgcttctgca tgccgccaga    60
cctcaggtgc agctggtgga gtctggggga ggcttggtac agcctggggg gtccctgaga   120
ctctcctgtg cagcctctgg attcaccttt accaaccatg ccatgagttg ggtccgccaga  180
gctccaggga aggggctgga gttggtctca agtattagtg gtaatggtcg taccacatac   240
tacgcagact ccgtgaaggg ccggttcacc atctccagag acatttccaa gaacacgctg   300
gatctgcaaa tgaacagcct gagagccgag gacacggccg tatattactg tgcgaaagat   360
gggggcgaaa ctctagttga ctccagaggc cagggcaccc tggtcaccgt ctcctcattc   420
gtgcccgtgt tcctgcctgc caagcctaca acaacccctg ctcctagacc tcctacacca   480
gctcctacaa tcgccagcca gcctctgtct ctgaggcctg aagcttgtag acctgctgct   540
ggcggagccg tgcataccag aggactggat ttcgcctgcg acatctacat ctgggcccct   600
ctggctggaa catgtggcgt tttgctgctg agcctcgtga tcaccctgta ctgcaaccac   660
cggaactgct ggctgaccaa gaagaagtac agcagcaggc tgcacgaccc caacggcgag   720
tacatgttca tgagggccgt gaacaccgcc aagaagagca ggctgaccga cgtgaccctg   780
agagtgaagt tcagcagatc cgccgatgcc cctgcctacc agcagggcca gaaccagctg   840
tacaacgagc tgaacctggg cagacgggaa gagtacgatg tgctggacaa aagacgtggc   900
cgggaccctg agatgggggg aaagccgaga ggaagaaccc tcaggaagg cctgtacaat    960
gaactgcaga agataagat ggcggaggcc tacagtgaga ttgggatgaa aggcgagcgc   1020
cggaggggca aggggcacga tggcctttac cagggtctca gtacagccac caaggacacc  1080
tacgacgccc ttcacatgca ggccctgccc cctcgctaa                         1119

SEQ ID NO: 38          moltype = DNA  length = 1122
FEATURE                Location/Qualifiers
misc_feature          1..1122
                      note = Synthetic
source                1..1122
                      mol_type = other DNA
                      organism = synthetic construct
SEQUENCE: 38
atggccctgc ctgttacagc tctgctgctg cctctggctc tgcttctgca tgccgccaga    60
cctcaggtgc agctggtgga gtctggggga ggcttggtac agcctggggg gtccctgaga   120
ctctcctgtg cagcctctgg attcaccttt agcagccatg ccatgacctg ggtccgccag   180
gctccgggga aggggctgga gtgggtcgca gctattagtg gcagtggtga tttcacacac   240
tacgcagact ccgtgaaggg ccggttcacc atctccagag acaattccaa gaacacggtg   300
tctctgcaaa tgaacaacct gagagccgag gacacggccg tatattactg tgcgaaagat   360
gaggatggtg ggagcttgct tggctacaga ggccagggca ccctggtcac cgtctcctca   420
ttcgtgcccg tgttcctgcc tgccaagcct acaacaaccc ctgctcctag acctcctaca   480
ccagctccta caatcgccag ccagcctctg tctctgaggc ctgaagcttg tagacctgct   540
gctggcggag ccgtgcatac cagaggactg gatttcgcct gcgacatcta catctgggcc   600
cctctggctg gaacatgtgg cgtttttgctg ctgagcctcg tgatcaccct gtactggcaac  660
caccggaact gctggctgac caagaagaag tacagcagca gcgtgcacga ccccaacggc   720
gagtacatgt tcatgagggc cgtgaacacc gccaagaaga gcaggctgac cgacgtgacc   780
ctgagagtga agttcagcag atccgccgat gcccctgcct accagcaggg ccagaaccag   840
ctgtacaacg agctgaacct gggcagacgg gaagagtacg atgtgctgga caaaagacgt   900
ggccgggacc ctgagatggg gggaaagccg agaaggaaga ccctcagga aggcctgtac    960
aatgaactgc agaaagataa gatggcggag gcctacagtg agattgggat gaaaggcgag  1020
cgccggaggg gcaagggggca cgatggcctt taccagggtc tcagtacagc caccaaggac  1080
acctacgacg cccttcacat gcaggccctg ccccctcgct aa                     1122

SEQ ID NO: 39          moltype = DNA  length = 1128
FEATURE                Location/Qualifiers
misc_feature          1..1128
                      note = Synthetic
source                1..1128
                      mol_type = other DNA
                      organism = synthetic construct
SEQUENCE: 39
atggccctgc ctgttacagc tctgctgctg cctctggctc tgcttctgca tgccgccaga    60
cctgaggtgc agctggtgga gtctggggga ggcttggtac agcctggggg gtccctgaga   120
ctctcctgtg cagcctctgg attcaccttt agcagctatg ccatgagctg ggtccgccag   180
gctccaggga aggggctgga gtgggtctca tctattagtg gtagtggtga ttacatatac   240
tacgcagact ccgtgaaggg ccggttcacc atctccagag acatatccaa gaacacgctg   300
tatctgcaaa tgaacagcct gagagccgag gacacggccg tatattactg tgcgaaagaa   360
ggtacgggtg ccaacagcag cttggcagac tacagaggcc agggcaccct ggtcaccgtc   420
tcctcattcg tgcccgtgtt cctgcctgcc aagcctacaa caaccctgc tcctagacct    480
cctacaccag ctcctacaat cgccagccag cctctgtctc tgaggcctga agcttgtaga   540
cctgctgctg gcggagccgt gcataccaga ggactggatt tcgcctgcga catctacatc   600
tgggcccctc tggctggaac atgtggcgtt ttgctgctga gcctcgtgat caccctgtac   660
tgcaaccacc ggaactgctg gctgaccaag aagaagtaca gcagcagcgt gcacgacccc   720
aacggcgagt acatgttcat gagggccgtg aacaccgcca agaagagcag gctgaccgac   780
gtgaccctga gagtgaagtt cagcagatcc gccgatgccc ctgcctacca gcagggccag   840
aaccagctgt acaacgagct gaacctgggc agacgggaag agtacgatgt gctggacaaa   900
agacgtggcg ggaccctga gatggggggga aagccgagag gaagaaccc tcaggaaggc    960
ctgtacaatg aactgcagaa agataagatg gcggaggcct acagtgagat tgggatgaaa  1020
```

-continued

```
ggcgagcgcc ggaggggcaa ggggcacgat ggcctttacc agggtctcag tacagccacc    1080
aaggacacct acgacgccct tcacatgcag gccctgcccc ctcgctaa                  1128

SEQ ID NO: 40          moltype = DNA  length = 1122
FEATURE                Location/Qualifiers
misc_feature           1..1122
                       note = Synthetic
source                 1..1122
                       mol_type = other DNA
                       organism = synthetic construct
SEQUENCE: 40
atggccctgc ctgttacagc tctgctgctg cctctggctc tgcttctgca tgccgccaga     60
cctgaggtgc agctgttgga gtctggggggg ggcttgatac agcctggggg gtccctgaga   120
ctctcctgtg cagcctctgg attcacctttt agcagccatg ccatgacctg ggtccgccag   180
gctccgggga aggggctgga gtgggtctca gctattagtg gtagtggtga ttacacacac   240
tacgcagact ccgtgaaggg tcggttcacc atctccagag acaattccaa gaacacggtg   300
tatctccaaa tgaacagtct gagagccgag gactcggccg tatattactg tgcgaaagat   360
gaggatggtg ggagcctcct ggggcacaga ggccagggca ccctggtcac cgtctcctca   420
ttcgtgcccg tgttcctgcc tgccaagcct acaacaaccc ctgctcctag acctcctaca   480
ccagctccta caatcgccag ccagcctctg tctctgaggc ctgaagcttg tagacctgct   540
gctggcggag ccgtgcatac cagaggactg gatttcgcct gcgacatcta catctgggcc   600
cctctggctg gaacatgtgg cgttttgctg ctgagcctcg tgatcaccct gtactgcaac   660
caccggaact gctggctgac caagaagaag tacagcagca gcgtgcacga ccccaacggc   720
gagtacatgt tcatgagggc cgtgaacacc gccaagaaga gcaggctgac cgacgtgacc   780
ctgagagtga agttcagcag atccgccgat gcccctgcct accagcaggg ccagaaccag   840
ctgtacaacg agctgaacct gggcagacgg gaagagtacg atgtgctgga caaaagacgt   900
ggccgggacc ctgagatggg gggaaagccg agaaggaaga accctcagga aggcctgtac   960
aatgaactgc agaaagataa gatggcggag gcctacagtg agattgggat gaaaggcgag   1020
cgccggaggg gcaaggggca cgatggcctt taccagggtc tcagtacagc caccaaggac   1080
acctacgacg cccttcacat gcaggccctg cccctcgct aa                       1122

SEQ ID NO: 41          moltype =   length =
SEQUENCE: 41
000

SEQ ID NO: 42          moltype = AA  length = 184
FEATURE                Location/Qualifiers
source                 1..184
                       mol_type = protein
                       organism = Homo sapiens
SEQUENCE: 42
MLQMAGQCSQ NEYFDSLLHA CIPCQLRCSS NTPPLTCQRY CNASVTNSVK GTNAILWTCL     60
GLSLIISLAV FVLMFLLRKI NSEPLKDEFK NTGSGLLGMA NIDLEKSRTG DEIILPRGLE    120
YTVEECTCED CIKSKPKVDS DHCFPLPAME EGATILVTTK TNDYCKSLPA ALSATEIEKS    180
ISAR                                                                184
```

40

The invention claimed is:

1. A chimeric antigen receptor (CAR) comprising an antigen recognition domain, a transmembrane (TM) domain, and an intracellular T-cell signaling domain, wherein the CAR has antigen specificity for B-cell maturation antigen (BCMA), wherein the antigen recognition domain comprises the amino acid sequences of SEQ ID NOs: 7-9.

2. The CAR of claim 1, wherein the antigen recognition domain does not comprise a linker peptide having a length of about 8 to about 40 amino acid residues.

3. The CAR of claim 1, wherein the CAR does not comprise an antibody light chain variable region.

4. The CAR of claim 1, wherein the antigen recognition domain comprises the amino acid sequence of SEQ ID NO: 15.

5. The CAR of claim 1, wherein the intracellular T-cell signaling domain comprises an intracellular T-cell signaling domain of any one of the following proteins: a human CD28 protein, a human CD3-zeta protein, a human FcRγ protein, a CD27 protein, an OX40 protein, a human 4-1BB protein, a human inducible T-cell costimulatory protein (ICOS), or any combination of the foregoing.

6. The CAR of claim 1 comprising the amino acid sequence of any one of SEQ ID NOs: 19, 23, and 27.

7. A pharmaceutical composition comprising the CAR of claim 1 and a pharmaceutically acceptable carrier.

8. An isolated host cell expressing the CAR of claim 1.

9. The isolated host cell of claim 8, wherein the host cell is a T-cell.

10. The isolated host cell of claim 8, wherein the host cell is a natural killer (NK) cell.

11. A population of cells comprising at least one host cell of claim 8.

12. A method of treating cancer in a mammal, the method comprising administering to the mammal the CAR of claim 1 in an amount effective to treat cancer in the mammal, wherein the cancer is a BCMA-expressing cancer.

13. The method of claim 12, wherein the cancer is multiple myeloma or Hodgkin's lymphoma.

\* \* \* \* \*